United States Patent
Lee et al.

(10) Patent No.: US 11,753,646 B2
(45) Date of Patent: Sep. 12, 2023

(54) FRUCTOSE-4-EPIMERASE AND METHOD OF PRODUCING TAGATOSE USING THE SAME

(71) Applicant: CJ CHEILJEDANG CORPORATION, Seoul (KR)

(72) Inventors: Young Mi Lee, Seoul (KR); Eul-Soo Park, Seoul (KR); Il Hyang Park, Seoul (KR); Sun Mi Shin, Seoul (KR); Sung Jae Yang, Seoul (KR); Ran Young Yoon, Seoul (KR); Eun Jung Choi, Seoul (KR); Seong Bo Kim, Seoul (KR); Seung Won Park, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 42 days.

(21) Appl. No.: 17/252,705

(22) PCT Filed: Sep. 27, 2019

(86) PCT No.: PCT/KR2019/012618
§ 371 (c)(1),
(2) Date: Dec. 15, 2020

(87) PCT Pub. No.: WO2020/067786
PCT Pub. Date: Apr. 2, 2020

(65) Prior Publication Data
US 2021/0363532 A1    Nov. 25, 2021

(30) Foreign Application Priority Data

Sep. 28, 2018 (KR) .................. 10-2018-0116609
Oct. 1, 2018 (KR) .................. 10-2018-0117237
Aug. 14, 2019 (KR) .................. 10-2019-0099827

(51) Int. Cl.
| | |
|---|---|
| *C12N 15/52* | (2006.01) |
| *C12N 9/88* | (2006.01) |
| *C12N 15/70* | (2006.01) |
| *C12P 19/02* | (2006.01) |

(52) U.S. Cl.
CPC ............ *C12N 15/52* (2013.01); *C12N 9/88* (2013.01); *C12N 15/70* (2013.01); *C12P 19/02* (2013.01); *C12Y 401/0204* (2013.01)

(58) Field of Classification Search
CPC .......... C12N 15/52; C12N 9/88; C12N 15/70; C12N 9/90; C12P 19/02; C12P 19/24; C12Y 401/0204
See application file for complete search history.

(56) References Cited

U.S. PATENT DOCUMENTS

| | | | |
|---|---|---|---|
| 2016/0186162 A1 | 6/2016 | Oh et al. | |
| 2020/0165639 A1* | 5/2020 | Zanghellini | ............... C12P 7/26 |

FOREIGN PATENT DOCUMENTS

| | | |
|---|---|---|
| EP | 3333260 A1 | 6/2018 |
| EP | 3604513 A1 | 2/2020 |
| EP | 3604514 A1 | 2/2020 |
| KR | 10-0964091 B1 | 6/2010 |
| KR | 10-1480422 B1 | 1/2015 |
| KR | 10-2015-0025703 A | 3/2015 |
| KR | 10-2015-0042391 A | 4/2015 |
| KR | 10-2016-0012001 | 2/2016 |
| WO | WO2017018863 A1 * | 2/2017 |

OTHER PUBLICATIONS

Whisstock et al. Quaterly Reviews of Biophysics, 2003, "Prediction of protein function from protein sequence and structure", 36(3): 307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10: 8-9. (Year: 2002).*
International search report and written opinion of PCT/KR2019/012618 dated Feb. 3, 2020, along with the English translation of the International search report; 10 pages.
Brinkkötter et al., "Two class II-tagatose-bisphosphate aldolases from enteric bacteria", Arch Microbiol, May 2002, vol. 177, pp. 410-419; DOI 10.1007/s00203-002-0406-6.
NCBI Reference Sequence: WP_015868068.1, "D-tagatose-bisphosphate aldolase, class II, non-catalytic subunit [Kosmotoga olearia]", Jul. 23, 2017; 1 page.
Lee et al., "Structure-based prediction and identification of 4-epimerization activity of phosphate sugars in class II aldolases", Scientific Reports | 7: 1934 | DOI:10.1038/s41598-017-02211-3; 9 pages.
Extended European Search Report for EP Application No. 19864869.3 dated Jun. 24, 2021; 7 pages.

* cited by examiner

*Primary Examiner* — Iqbal H Chowdhury
(74) *Attorney, Agent, or Firm* — Squire Patton Boggs (US) LLP

(57) ABSTRACT

Provided are a tagatose-bisphosphate aldolase variant having tagatose conversion activity, and a method of preparing tagatose using the same.

8 Claims, 3 Drawing Sheets
Specification includes a Sequence Listing.

[FIG. 1]
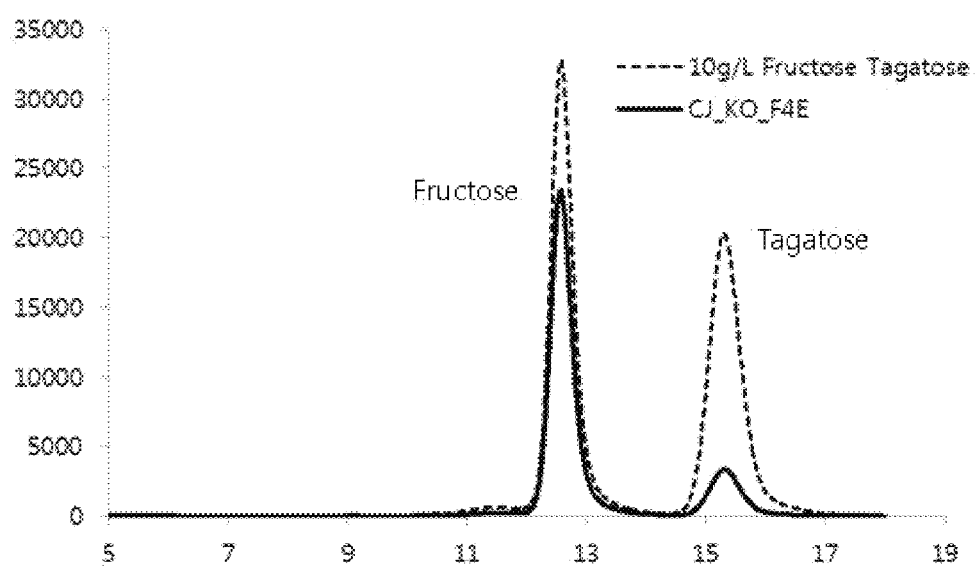

[FIG. 2]
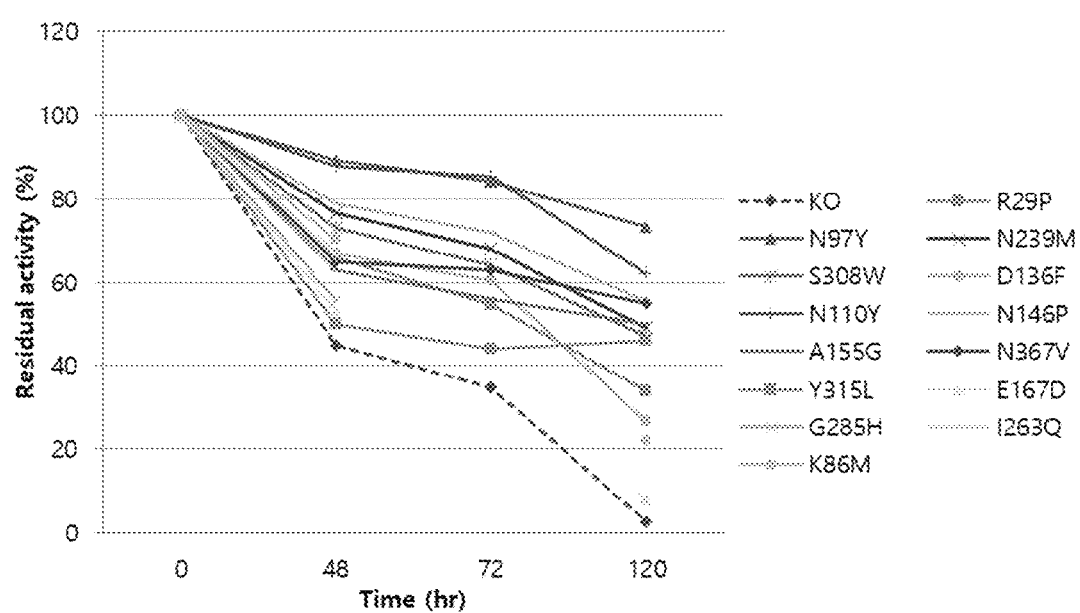

[FIG. 3]
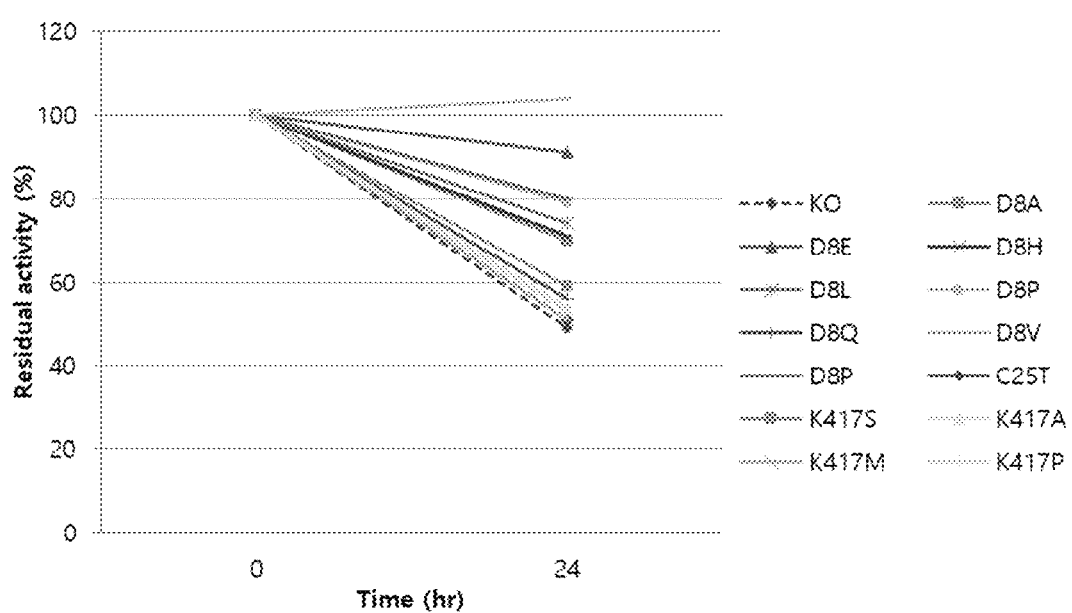

FRUCTOSE-4-EPIMERASE AND METHOD OF PRODUCING TAGATOSE USING THE SAME

This application incorporates by reference the computer readable sequence listing in the file "059520_00019_ST25.txt," created Dec. 9, 2020, having 68.3 KB.

TECHNICAL FIELD

The present disclosure relates to a fructose-4-epimerase variant having improved conversion activity or stability, and a method of preparing tagatose using the same.

BACKGROUND ART

Tagatose has a natural sweet taste hardly distinguishable from sucrose and also has physical properties similar to sucrose. Tagatose is a natural sweetener, which is present in a small amount in food such as milk, cheese, cacao, etc., and in sweet fruits such as apples and mandarin. Tagatose has a calorie value of 1.5 kcal/g which is one third that of sucrose, and a glycemic index (GI) of 3 which is 5% that of sucrose. Tagatose has a sweet taste similar to that of sucrose and various health benefits. In this regard, tagatose may be used as an alternative sweetener capable of satisfying both health and taste when applied to a wide variety of products.

Conventional known methods of producing tagatose include a chemical method (a catalytic reaction) and a biological method (an isomerizing enzyme reaction) of using galactose as a main raw material (see Korean Patent No. 10-0964091). In order to economically obtain galactose as a raw material for the above reactions, studies have been conducted on various basic raw materials containing galactose, and a method of obtaining galactose therefrom to produce tagatose. A representative basic raw material for obtaining galactose is lactose. However, the price of lactose or lactose-containing products was unstable, depending on produced amounts, supply and demand of raw milk and lactose in global markets, etc. Thus, there is a limitation in the stable supply of the raw material for tagatose production. Accordingly, there is a demand for a new method capable of producing tagatose using common saccharides (sucrose, glucose, fructose, etc.).

DISCLOSURE

Technical Problem

The present inventors have developed a novel variant protein including one or more amino acid substitutions in an amino acid sequence of SEQ ID NO: 1, and they found that the variant protein has conversion activity identical to that of the wild-type of SEQ ID NO: 1, or has improved conversion activity or stability and improved tagatose productivity, as compared with the wild-type, thereby completing the present disclosure.

Technical Solution

An object of the present disclosure is to provide a fructose-4-epimerase variant, in which one or more amino acid residues are substituted in fructose-4-epimerase including an amino acid sequence of SEQ ID NO: 1.

Another object of the present disclosure is to provide a polynucleotide encoding the fructose-4-epimerase variant.

Still another object of the present disclosure is to provide a vector including the polynucleotide.

Still another object of the present disclosure is to provide a microorganism including the variant.

Still another object of the present disclosure is to provide a composition for producing tagatose, the composition including one or more of fructose-4-epimerase or the fructose-4-epimerase variant; the microorganism including the same; or a culture of the microorganism.

Still another object of the present disclosure is to provide a method of preparing tagatose, the method including the step of reacting fructose in the presence of fructose-4-epimerase or the fructose-4-epimerase variant; the microorganism expressing the same; the culture of the microorganism, or the fructose-4-epimerase derived therefrom.

Advantageous Effects

A fructose-4-epimerase variant of the present disclosure enables industrial scale production of tagatose having excellent characteristics, and converts fructose, which is a common saccharide, into tagatose, thereby exhibiting a high economical effect.

DESCRIPTION OF DRAWINGS

FIG. 1 shows HPLC chromatography results showing that tagatose-bisphosphate aldolase (CJ_KO_F4E) prepared in one embodiment of the present disclosure has fructose-4-epimerase activity; and FIGS. 2 and 3 show graphs showing relative values of residual activity over time under a temperature condition of 60° C. in order to evaluate thermal stability of variants.

BEST MODE

The present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

To achieve the objects, one aspect of the present disclosure provides a fructose-4-epimerase variant including one or more amino acid substitutions in an amino acid sequence of fructose-4-epimerase.

To achieve the objects, another aspect of the present disclosure provides a fructose-4-epimerase variant including one or more amino acid substitutions in an amino acid sequence of SEQ ID NO: 1.

As used herein, the term "fructose-4-epimerase" is an enzyme having fructose-4-epimerization activity to convert fructose into tagatose by epimerization at C4 position of fructose. With respect to the objects of the present disclosure, fructose-4-epimerase may include any enzyme without limitation, as long as it is able to produce tagatose using fructose as a substrate, and it may be used interchangeably with 'D-fructose C4-epimerase'. For example, the fructose-4-epimerase may include tagatose bisphosphate aldolase or tagatose-bisphosphate aldolase class II accessory protein belonging to EC 4.1.2.40 in a known database KEGG (Kyoto Encyclopedia of Genes and Genomes), as long as it has activity to convert fructose as a substrate into tagatose. The tagatose-bisphosphate aldolase is known as an enzyme that produces glycerone phosphate and D-glyceraldehyde 3-phosphate from D-tagatose 1,6-bisphosphate as a substrate, as in the following [Reaction Scheme 1].

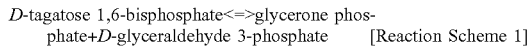

D-tagatose 1,6-bisphosphate<=>glycerone phosphate+D-glyceraldehyde 3-phosphate    [Reaction Scheme 1]

For example, the fructose-4-epimerase may include tagatose-6-phosphate kinase (EC 2.7.1.144), as long as it has activity to convert fructose as a substrate into tagatose. The tagatose-6-phosphate kinase is known as an enzyme that produces ADP and D-tagatose 1,6-bisphosphate from ATP and D-tagatose 6-phosphate as a substrate, as in the following [Reaction Scheme 2].

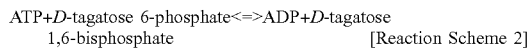

ATP+D-tagatose 6-phosphate<=>ADP+D-tagatose 1,6-bisphosphate    [Reaction Scheme 2]

The activity of fructose-4-epimerase may have a conversion rate of tagatose from fructose as a substrate (conversion rate=tagatose weight/initial fructose weight*100) of 0.01% or more, specifically 0.1% or more, and more specifically 0.3% or more. Much more specifically, the conversion rate may be in the range of 0.01% to 100% or in the range of 0.1% to 50%.

The fructose-4-epimerase, tagatose-bisphosphate aldolase, or tagatose-6-phosphate kinase of the present disclosure may be an enzyme derived from a heat-resistant microorganism or a variant thereof, for example, an enzyme derived from *Kosmotoga olearia, Thermanaerothrix daxensis, Rhodothermus profundi, Rhodothermus marinus, Limnochorda pilosa, Caldithrix abyssi, Caldilinea aerophila, Thermoanaerobacter thermohydrosulfuricus, Acidobacteriales bacterium, Caldicellulosiruptor kronotskyensis, Thermoanaerobacterium thermosaccharolyticum*, or *Pseudoalteromonas* sp. H103, or a variant thereof, but is not limited thereto, specifically, an enzyme derived from *Kosmotoga olearia* (SEQ ID NO: 1), *Thermoanaerobacterium thermosaccharolyticum* (SEQ ID NO: 3), *Pseudoalteromonas* sp. H103 (SEQ ID NO: 5), *Thermanaerothrix daxensis* (SEQ ID NO: 7), *Acidobacteriales bacterium* (SEQ ID NO: 9), *Rhodothermus profundi* (SEQ ID NO: 11), *Rhodothermus marinus* (SEQ ID NO: 13), *Limnochorda pilosa* (SEQ ID NO: 15), *Caldithrix abyssi* (SEQ ID NO: 17), *Caldicellulosiruptor kronotskyensis* (SEQ ID NO: 19), *Caldilinea* aerophila (SEQ ID NO: 21), or *Thermoanaerobacter thermohydrosulfuricus* (SEQ ID NO: 23), or a variant thereof, but is not limited thereto.

Specifically, the fructose-4-epimerase, tagatose-bisphosphate aldolase, or tagatose-6-phosphate kinase may include an amino acid sequence of SEQ ID NO: 1, 3, 5, 7, 9, 11, 13, 15, 17, 19, 21, or 23, or an amino acid sequence having 70% or higher homology or identity thereto, but is not limited thereto. More specifically, the fructose-4-epimerase of the present disclosure may include a polypeptide having at least 60%, 70%, 80%, 85%, 90%, 95%, 96%, 97%, 98%, or 99% homology or identity to the amino acid sequence of SEQ ID NO: 1, 3, 5, 7, 9, 11, 13, 15, 17, 19, 21, or 23. Further, it is apparent that an accessory protein having an amino acid sequence having the homology or identity and exhibiting the efficacy corresponding to the above protein is also included in the scope of the present disclosure, although a partial sequence of the amino acid sequence is deleted, modified, substituted, or added.

In the present disclosure, SEQ ID NO: 1 means an amino acid sequence having fructose-4-epimerase activity. The sequence of SEQ ID NO: 1 may be obtained from a known database, GenBank of NCBI or KEGG (Kyoto Encyclopedia of Genes and Genomes). For example, the sequence may be derived from *Kosmotoga olearia*, more specifically, a polypeptide/protein including the amino acid sequence of SEQ ID NO: 1, but is not limited thereto. Further, a sequence having activity identical to the above amino acid sequence may be included without limitation. Further, the amino acid sequence of SEQ ID NO: 1 or an amino acid sequence having 70% or higher homology or identity thereto may be included, but is not limited thereto. Specifically, the amino acid sequence may include the amino acid sequence having SEQ ID NO: 1 and an amino acid sequence having at least 70%, 80%, 85%, 90%, 95%, 96%, 97%, 98%, or 99% or higher homology or identity to SEQ ID NO: 1. Further, it is apparent that a protein having an amino acid sequence having the homology or identity and exhibiting the efficacy corresponding to the above protein is also included in the scope of the present disclosure, although a partial sequence of the amino acid sequence is deleted, modified, substituted, or added.

That is, although described as "a protein having an amino acid sequence of a particular SEQ ID NO" in the present disclosure, the protein may have an activity that is identical or similar to that of a protein consisting of an amino acid sequence of the corresponding SEQ ID NO. In such a case, it is obvious that any proteins having an amino acid sequence with deletion, modification, substitution, conservative substitution, or addition in part of the sequence also can be used in the present disclosure. For example, in the case of having the activity that is the same as or corresponding to that of the modified protein, it does not exclude an addition of a sequence upstream or downstream of the amino acid sequence, which does not alter the function of the protein, a mutation that may occur naturally, a silent mutation thereof, or a conservative constitution, and even when the sequence addition or mutation is present, it obviously belongs to the scope of the present disclosure.

As used herein, the term "tagatose" is, a kind of ketohexose which is a monosaccharide, used interchangeably with "D-tagatose"

As used herein, the term "fructose-4-epimerase variant" means a fructose-4-epimerase variant including one or more amino acid substitutions in the amino acid sequence of the polypeptide having fructose-4-epimerase activity.

Specifically, the amino acid substitution may include substitution of another amino acid for an amino acid at one or more positions selected from the group consisting of positions 8, 20, 23, 25, 26, 29, 45, 51, 53, 63, 86, 91, 97, 110, 133, 144, 146, 151, 155, 167, 172, 173, 174, 181, 191, 239, 263, 266, 285, 294, 298, 308, 315, 316, 317, 323, 336, 347, 359, 367, 385, 386, 388, 389, 410, 414, and 417 from the N-terminus, but is not limited thereto.

As used herein, 'position N' may include position N and an amino acid position corresponding to the position N, specifically, an amino acid position corresponding to any amino acid residue in a mature polypeptide disclosed in a particular amino acid sequence. The particular amino acid sequence may be any one of the amino acid sequences of SEQ ID NOS: 1, 3, 5, 7, 9, 11, 13, 15, 17, 19, 21, and 23.

The amino acid position corresponding to the position N or the amino acid position corresponding to any amino acid residue in the mature polypeptide disclosed in the particular amino acid sequence may be determined using the Needleman-Wunsch algorithm (literature [Needleman and Wunsch, 1970, J. Mol. Biol. 48: 443-453]), specifically, version 5.0.0 or later, as implemented in the Needle program of the EMBOSS package (EMBOSS: The European Molecular Biology Open Software Suite, literature [Rice et al., 2000, Trends Genet. 16:276-277]). Parameters used may be gap open penalty of 10, gap extension penalty of 0.5, and EBLOSUM62 (EMBOSS version of BLOSUM62) substitution matrix.

Identification of the amino acid residue at the amino acid position corresponding to the position N or at the amino acid position corresponding to any amino acid residue in the mature polypeptide disclosed in the particular amino acid sequence may be determined by alignment of multiple polypeptide sequences using several computer programs including, but not limited to, MUSCLE (multiple sequence comparison by log-expectation; version 3.5 or later; literature [Edgar, 2004, Nucleic Acids Research 32: 1792-1797]), MAFFT (version 6.857 or later; literature [Katoh and Kuma, 2002, Nucleic Acids Research 30: 3059-3066]; literature [Katoh et al., 2005, Nucleic Acids Research 33: 511-518]; literature [Katoh and Toh, 2007, Bioinformatics 23: 372-374]; literature [Katoh et al., 2009, Methods in Molecular Biology 537: 39-64]; literature [Katoh and Toh, 2010, Bioinformatics 26: 1899-1900]), and EMBOSS EMMA employing ClustalW (1.83 or later; literature [Thompson et al., 1994, Nucleic Acids Research 22: 4673-4680]), using their respective default parameters.

When the other polypeptide has diverged from the mature polypeptide of the particular amino acid sequence such that traditional sequence-based comparison fails to detect their relationship (literature [Lindahl and Elofsson, 2000, J. Mol. Biol. 295: 613-615]), other pairwise sequence comparison algorithms may be used. Greater sensitivity in sequence-based searching may be attained using search programs that utilize probabilistic representations of polypeptide families (profiles) to search databases. For example, PSI-BLAST program generates profiles through an iterative database search process and is capable of detecting remote homologs (literature [Atschul et al., 1997, Nucleic Acids Res. 25: 3389-3402]). Even greater sensitivity may be achieved if the family or superfamily for the polypeptide has one or more representatives in the protein structure databases. Programs such as GenTHREADER (literature [Jones, 1999, J. Mol. Biol. 287: 797-815]; literature [McGuffin and Jones, 2003, Bioinformatics 19: 874-881]) utilize information from a variety of sources (PSI-BLAST, secondary structure prediction, structural alignment profiles, and solvation potentials) as input to a neural network that predicts the structural folding for a query sequence. Similarly, the method of literature [Gough et al., 2000, J. Mol. Biol. 313: 903-919] may be used to align a sequence of unknown structure with the superfamily models present in the SCOP database. These alignments may in turn be used to generate homology, similarity, or identity models for the polypeptide, and such models may be assessed for accuracy using a variety of tools developed for that purpose.

The 'another polypeptide' is not limited, as long as it is an amino acid other than the amino acid corresponding to the position. 'Amino acids' are classified into four types of acidic, basic, polar (hydrophilic), and nonpolar (hydrophobic) amino acids according to properties of their side chains.

The variant may be a protein having substitution of one or more amino acids selected from the group consisting of nonpolar amino acids including glycine (G), alanine (A), valine (V), leucine (L), isoleucine (I), methionine (M), phenylalanine (F), tryptophan (W), and proline (P); polar amino acids including serine (S), threonine (T), cysteine (C), tyrosine (Y), aspartic acid (D), and glutamine (Q); acidic amino acids including asparagine (N) and glutamic acid (E); and basic amino acids including lysine (K), arginine (R), and histidine (H) for an amino acid at each position of the amino acid sequence of SEQ ID NO: 1, but is not limited thereto.

Specifically, the amino acid at position 8 may be substituted by a nonpolar amino acid, a polar amino acid, an acidic amino acid, or a basic amino acid, more specifically, alanine (A), glutamic acid (E), histidine (H), leucine (L), proline (P), glutamine (Q), or valine (V). The amino acid at position 20 may be substituted by a basic amino acid, more specifically, arginine (R). The amino acid at position 23 may be substituted by a polar amino acid, more specifically, cysteine (C). The amino acid at position 25 may be substituted by a nonpolar amino acid, a polar amino acid, an acidic amino acid, or a basic amino acid, more specifically, alanine (A), valine (V), serine (S), aspartic acid (D), histidine (H), phenylalanine (F), leucine (L), glycine (G), asparagine (N), methionine (M), glutamic acid (E), glutamine (Q), proline (P), lysine (K), tyrosine (Y), arginine (R), tryptophan (W), isoleucine (I), or threonine (T). The amino acid at position 26 may be substituted by a nonpolar amino acid, or a polar amino acid, more specifically, alanine (A), threonine (T) or valine (V). The amino acid at position 29 may be substituted by a nonpolar amino acid, a polar amino acid, an acidic amino acid, or a basic amino acid, more specifically, tryptophan (W), cysteine (C), lysine (K), alanine (A), glutamic acid (E), leucine (L), proline (P), glutamine (Q), serine (S) or valine (V). The amino acid at position 45 may be substituted by a nonpolar amino acid, a polar amino acid, an acidic amino acid, or a basic amino acid, more specifically, alanine (A), glutamine (Q), valine (V), lysine (K), glutamic acid (E), or methionine (M). The amino acid at position 51 may be substituted by a nonpolar amino acid, a polar amino acid, an acidic amino acid, or a basic amino acid, more specifically, glycine (G), alanine (A), valine (V), leucine (L), isoleucine (I), methionine (M), phenylalanine (F), tryptophan (W), proline (P), serine (S), cysteine (C), tyrosine (Y), aspartic acid (D), glutamine (Q), asparagine (N), glutamic acid (E), lysine (K), arginine (R), or histidine (H). The amino acid at position 53 may be substituted by a nonpolar amino acid, a polar amino acid, or a basic amino acid, more specifically, tryptophan (W), phenylalanine (F), cysteine (C), lysine (K), arginine (R), glycine (G), serine (S), leucine (L), threonine (T), or proline (P). The amino acid at position 63 may be substituted by a nonpolar amino acid, a polar amino acid, or an acidic amino acid, more specifically, proline (P), alanine (A), methionine (M), valine (V), glutamic acid (E), or leucine (L), and the amino acid at position 86 may be substituted by a nonpolar amino acid, a polar amino acid, or a basic amino acid, more specifically, arginine (R), valine (V), methionine (M), alanine (A), leucine (L), or glycine (G). The amino acid at position 91 may be substituted by a nonpolar amino acid, or a polar amino acid, more specifically, phenylalanine (F), tryptophan (W), or tyrosine (Y). The amino acid at position 97 may be substituted by a nonpolar amino acid, a polar amino acid, an acidic amino acid, or a basic amino acid, more specifically, leucine (L), proline (P), tyrosine (Y), glutamic acid (E), lysine (K). The amino acid at position 110 may be substituted by a polar amino acid, more specifically, tyrosine (Y). The amino acid at position 133 may be substituted by a nonpolar amino acid, a polar amino acid, an acidic amino acid, or a basic amino acid, more specifically, valine (V), leucine (L), proline (P), glutamine (Q), asparagine (N), or glutamic acid (E). The amino acid at position 144 may be substituted by a nonpolar amino acid, or a polar amino acid, more specifically, alanine (A), valine (V), isoleucine (I), phenylalanine (F), or serine (S). The amino acid at position 146 may be substituted by a nonpolar amino acid, a polar amino acid, or a basic amino acid, more specifically, leucine (L), isoleucine (I), proline (P), glutamine (Q), or histidine (H). The amino acid at position 151 may be substituted by a nonpolar amino acid, more specifically, glycine (G). The amino acid at position 155 may be substituted by a nonpolar amino acid, more specifically, glycine (G). The amino acid at position 167 may be substituted by a nonpolar amino acid, a polar amino acid, or a basic amino acid, more specifically, valine (V), glycine (G), alanine (A), arginine (R), leucine (L), threonine (T), aspartic acid (D). The amino acid at position 172 may be substituted by a nonpolar amino acid, more specifically, alanine (A), or threonine (T). The amino acid at position 173 may be substituted by a nonpolar amino acid, a polar amino acid, or an acidic amino acid, more specifically, alanine (A), valine (V), threonine (T), glutamic acid (E) or aspartic acid (D). The amino acid at position 174 may be substituted by a nonpolar amino acid, a polar amino acid, or a basic amino acid, more specifically, glycine (G), valine (V), leucine (L), methionine (M), phenylalanine (F), tryptophan (W), serine (S), tyrosine (Y), aspartic acid (D), lysine (K), or arginine (R). The amino acid at position 181 may be substituted by a nonpolar amino acid, or a basic amino acid, more specifically, glycine (G), alanine (A), leucine (L), isoleucine (I), proline (P), lysine (K), or arginine (R). The amino acid at position 191 may be substituted by a nonpolar amino acid, a polar amino acid, or a basic amino acid, more specifically, glycine (G), alanine (A), valine (V), leucine (L), isoleucine (I), serine (S), threonine (T), or arginine (R). The amino acid at position 239 may be substituted by a nonpolar amino acid, an acidic amino acid, or a basic amino acid, more specifically, glycine (G), alanine (A), valine (V), leucine (L), tryptophan (W), proline (P), glutamic acid (E), or lysine (K). The amino acid at position 263 may be substituted by a nonpolar amino acid, a polar amino acid, an acidic amino acid, or a basic amino acid, more specifically, alanine (A), leucine (L), glutamine (Q), glutamic acid (E), or lysine (K). The amino acid at position 266 may be substituted by a nonpolar amino acid, a polar amino acid, or a basic amino acid, more specifically, glycine (G), alanine (A), valine (V), leucine (L), isoleucine (I), tryptophan (W), proline (P), cysteine (C), tyrosine (Y), aspartic acid (D), or arginine (R). The amino acid at position 285 may be substituted by a nonpolar amino acid, a polar amino acid, or an acidic amino acid, more specifically, valine (V), leucine (L), methionine (M), tyrosine (Y), aspartic acid (D), glutamine (Q), or glutamic acid (E). The amino acid at position 294 may be substituted by a nonpolar amino acid, more specifically, glycine (G). The amino acid at position 298 may be substituted by a nonpolar amino acid, more specifically, glycine (G). The amino acid at position 308 may be substituted by a nonpolar amino acid, or a basic amino acid, more specifically, alanine (A), valine (V), leucine (L), isoleucine (I), tryptophan (W), arginine (R), or histidine (H). The amino acid at position 315 may be substituted by a nonpolar amino acid, a polar amino acid, or a basic amino acid, more specifically, alanine (A), valine (V), leucine (L), proline (P), aspartic acid (D), or histidine (H). The amino acid at position 316 may be substituted by a nonpolar amino acid, a polar amino acid, an acidic amino acid, or a basic amino acid, more specifically, valine (V), leucine (L), methionine (M), proline (P), threonine (T), asparagine (N), lysine (K), or arginine (R). The amino acid at position 317 may be substituted by a nonpolar amino acid, a polar amino acid, or a basic amino acid, more specifically, valine (V), isoleucine (I), serine (S), aspartic acid (D), arginine (R), or histidine (H). The amino acid at position 323 may be substituted by a nonpolar amino acid, a polar amino acid, or a basic amino acid, more specifically, glycine (G), valine (V), leucine (L), methionine (M), aspartic acid (D), arginine (R), or histidine (H). The amino acid at position 336 may be substituted by a nonpolar amino acid, or a basic amino acid, more specifically, glycine (G), alanine (A), or arginine (R). The amino acid at position 347 may be substituted by a nonpolar amino acid, a polar amino acid, or an acidic amino acid, more specifically, glycine (G), proline (P), serine (S), tyrosine (Y), aspartic acid (D), asparagine (N), or phenylalanine (F). The amino acid at position 359 may be substituted by a nonpolar amino acid, a polar amino acid, an acidic amino acid, or a basic amino acid, more specifically, glycine (G), alanine (A), valine (V), aspartic acid (D), asparagine (N), or arginine (R). The amino acid at position 367 may be substituted by a nonpolar amino acid, or a basic amino acid, more specifically, glycine (G), alanine (A), valine (V), leucine (L), isoleucine (I), or arginine (R). The amino acid at position 385 may be substituted by a nonpolar amino acid, or a basic amino acid, more specifically, alanine (A), or arginine (R). The amino acid at position 386 may be substituted by a nonpolar amino acid, a polar amino acid, or a basic amino acid, more specifically, alanine (A), valine (V), leucine (L), isoleucine (I), serine (S), threonine (T), aspartic acid (D), arginine (R), or histidine (H). The amino acid at position 388 may be substituted by a nonpolar amino acid, a polar amino acid, or a basic amino acid, more specifically, glycine (G), valine (V), isoleucine (I), serine (S), threonine (T), aspartic acid (D), or arginine (R). The amino acid at position 389 may be substituted by a nonpolar amino acid, a polar amino acid, an acidic amino acid, or a basic amino acid, more specifically, glycine (G), valine (V), methionine (M), serine (S), aspartic acid (D), glutamic acid (E), lysine (K), or arginine (R). The amino acid at position 410 may be substituted by a nonpolar amino acid, more specifically, alanine (A), valine (V), leucine (L), or threonine (T). The amino acid at position 414 may be substituted by a nonpolar amino acid, a polar amino acid, or an acidic amino acid, more specifically, proline (P), glutamine (Q), or glutamic acid (E). The amino acid at position 417 may be substituted by a nonpolar amino acid, a polar amino acid, or a basic amino acid, more specifically, glycine (G), alanine (A), valine (V), leucine (L), methionine (M), proline (P), serine (S), aspartic acid (D), or arginine (R), but is not limited thereto.

The fructose-4-epimerase variant may include a polypeptide, of which one or more amino acids differ from the recited sequence in conservative substitutions and/or modifications, in addition to substitution of another amino acid for the amino acid at the particular position, while retaining functions or properties of the protein.

As used herein, the term "conservative substitution" means substitution of one amino acid with another amino acid that has similar structural and/or chemical properties. The variant may have, for example, one or more conservative substitutions while retaining one or more biological activities. The conservative substitution has little or no impact on the activity of a resulting polypeptide.

Further, variants having variation of one or more amino acids in addition to the amino acids at the above-described particular positions may include deletion or addition of amino acids that have minimal influence on properties and a secondary structure of the polypeptide. For example, a polypeptide may be conjugated to a signal (or leader) sequence at the N-terminus of the protein, which co-translationally or post-translationally directs transfer of the protein. The polypeptide may also be conjugated to other sequence or a linker for identification, purification, or synthesis of the polypeptide.

Further, the variant includes the above-described variations of SEQ ID NO: 1 and/or amino acids having at least 70%, 80%, 85%, 90%, 95%, 96%, 97%, 98%, or 99% or higher homology or identity to SEQ ID NO: 1 other than the variations and positions of SEQ ID NO: 1. The variations of SEQ ID NO: 1 are as described above, and homology or identity thereto may be homology or identity at positions other than the above-described variations.

With respect to the objects of the present disclosure, the fructose-4-epimerase variant is characterized by having improved conversion activity or stability, as compared with the wild-type.

The term "conversion activity" means conversion into tagatose by epimerizing D-fructose at C4 position. The term "stability" means having thermal stability of an enzyme having high heat resistance.

Specifically, the fructose-4-epimerase variant is characterized in that its activity to convert into tagatose by epimerizing D-fructose at C4 position and/or stability are/is improved, as compared with the wild-type of SEQ ID NO: 1.

For example, the fructose-4-epimerase variant of the present disclosure may be an enzyme having high heat resistance. Specifically, the fructose-4-epimerase variant of the present disclosure may exhibit 50% to 100%, 60% to 100%, 70% to 100%, or 75% to 100% activity of the maximum activity at 50° C. to 70° C. More specifically, the fructose-4-epimerase variant of the present disclosure may exhibit 80% to 100% or 85% to 100% activity of the maximum activity at 55° C. to 60° C., 60° C. to 70° C., 55° C., 60° C., or 70° C.

Examples of the mutation sites and mutated amino acids of the variant are as described in Tables 1 to 6, but are not limited thereto.

Another aspect of the present disclosure provides a polynucleotide encoding the fructose-4-epimerase variant, or a vector including the polynucleotide.

As used herein, the term "polynucleotide" refers to a DNA or RNA strand having a predetermined length or more, which is a long chain polymer of nucleotides formed by linking nucleotide monomers via covalent bonds. More specifically, the polynucleotide refers to a polynucleotide fragment encoding the variant protein.

The polynucleotide encoding the fructose-4-epimerase variant of the present disclosure may include any polynucleotide sequence without limitation, as long as it is a polynucleotide sequence encoding the fructose-4-epimerase variant of the present disclosure. For example, the polynucleotide encoding the fructose-4-epimerase variant of the present disclosure may be a polynucleotide sequence encoding the amino acid sequence, but is not limited thereto. In the polynucleotide, various modifications may be made in the coding region provided that they do not change the amino acid sequence of the protein, due to codon degeneracy or in consideration of the codons preferred by the organism in which the protein is to be expressed. Therefore, it is apparent that, due to codon degeneracy, a polynucleotide which may be translated into the polypeptide composed of the amino acid sequence or the polypeptide having homology or identity thereto may also be included.

Further, a probe which may be produced from a known nucleotide sequence, for example, a sequence which hybridizes with a complementary sequence to all or a part of the nucleotide sequence under stringent conditions to encode the fructose-4-epimerase variant may also be included without limitation.

The term "stringent conditions" mean conditions under which specific hybridization between polynucleotides is allowed. Such conditions are described in detail in a literature (e.g., J. Sambrook et al., supra). For example, the stringent conditions may include, for example, conditions under which genes having high homology or identity, 70% or higher, 80% or higher, 85% or higher, specifically 90% or higher, more specifically 95% or higher, much more specifically 97% or higher, particularly specifically 99% or higher homology or identity are hybridized with each other and genes having homology or identity lower than the above homology or identity are not hybridized with each other, or ordinary washing conditions of Southern hybridization, i.e., washing once, specifically, twice or three times at a salt concentration and a temperature corresponding to 60° C., 1×SSC, 0.1% SDS, specifically, 60° C., 0.1×SSC, 0.1% SDS, and more specifically 68° C., 0.1×SSC, 0.1% SDS.

Although a mismatch between nucleotides may occur due to the stringency of hybridization, it is required that the two nucleic acids have a complementary sequence. The term "complementary" is used to describe the relationship between nucleotide bases which may hybridize with each other. For example, with regard to DNA, adenosine is complementary to thymine and cytosine is complementary to guanine. Accordingly, the present disclosure may include not only the substantially similar nucleic acid sequences but also isolated nucleic acid fragments which are complementary to the entire sequence.

Specifically, the polynucleotide having homology or identity may be detected using hybridization conditions including the hybridization step at a Tm value of 55° C. and the conditions described above. Additionally, the Tm value may be 60° C., 63° C., or 65° C., but is not limited thereto, and may be appropriately controlled by one of ordinary skill in the art according to the purposes.

Appropriate stringency for the hybridization of polynucleotides depends on the length and degree of complementarity of the polynucleotides, and the variables are well-known in the art (see Sambrook et al., supra, 9.50-9.51, 11.7-11.8).

As used herein, the term 'homology' or 'identity' means the degree of relevance between two given amino acid sequences or nucleotide sequences, and may be expressed as a percentage.

The terms 'homology' and 'identity' may be often used interchangeably.

The sequence homology or identity of the conserved polynucleotide or polypeptide may be determined by standard alignment algorithms, and may be used with default gap penalties established by the used program. Substantially, homologous or identical sequences may hybridize under moderately or highly stringent conditions such that the full length of the sequence or at least about 50%, 60%, 70%, 80%, or 90% or more of the full-length may hybridize. Also, contemplated are polynucleotides that contain degenerate codons in place of codons in the hybridization.

Whether or not any two polynucleotide or polypeptide sequences have homology, similarity, or identity may be determined using known computer algorithms such as the "FASTA" program, using, for example, the default parameters as in Pearson et al (1988)[Proc. Natl. Acad. Sci. USA 85]: 2444], or determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277) (version 5.0.0 or later) (including GCG program package (Devereux, J., et al, Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.] (1988) SIAM J Applied Math 48: 1073). For example, BLAST of the National Center for Biotechnology Information database, or ClustalW may be used to determine homology, similarity, or identity.

Homology, similarity, or identity of polynucleotides or polypeptides may be determined, for example, by comparing sequence information using a GAP computer program such as Needleman et al. (1970), J Mol Biol. 48: 443, as disclosed in Smith and Waterman, Adv. Appl. Math (1981) 2:482. Briefly, the GAP program defines similarity as the number of aligned symbols (i.e., nucleotides or amino acids), which are similar, divided by the total number of symbols in the shorter of the two sequences. Default parameters for the GAP program may include: (1) a binary comparison matrix (containing a value of 1 for identities and 0 for non-identities) and the weighted comparison matrix of Gribskov et al (1986) Nucl. Acids Res. 14: 6745, as disclosed in Schwartz and Dayhoff, eds., Atlas Of Protein Sequence And Structure, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or gap open penalty of 10, gap extension penalty of 0.5); and (3) no penalty for end gaps. Therefore, as used herein, the term "homology" or "identity" represents relevance between sequences.

As used herein, the term "vector" means a DNA construct that includes a nucleotide sequence of a polynucleotide encoding a target variant protein operably linked to an appropriate regulatory sequence to enable expression of the target variant protein in an appropriate host cell. The regulatory sequence may include a promoter capable of initiating transcription, any operator sequence for the regulation of such transcription, a sequence of an appropriate mRNA ribosome-binding domain, and a sequence regulating termination of transcription and translation. After the vector is transformed into the appropriate host cell, it may replicate or function independently of the host genome, and may be integrated into the genome itself.

The vector used in the present disclosure is not particularly limited, as long as it is able to replicate in the host cell, and any vector known in the art may be used. Examples of commonly used vectors may include a natural or recombinant plasmid, cosmid, virus, and bacteriophage. For instance, pWE15, M13, MBL3, MBL4, IXII, ASHII, APII, t10, t11, Charon4A, Charon21A, etc. may be used as a phage vector or cosmid vector. As a plasmid vector, pBR type, pUC type, pBluescriptII type, pGEM type, pTZ type, pCL type, pET type, etc. may be used. Specifically, pDZ, pACYC177, pACYC184, pCL, pECCG117, pUC19, pBR322, pMW118, pCC1BAC vector, etc. may be used.

For example, a polynucleotide encoding a target variant protein in the chromosome may be replaced by a mutated polynucleotide using a vector for intracellular chromosomal insertion. The chromosomal insertion of the polynucleotide may be performed by any method known in the art, for example, homologous recombination, but is not limited thereto. A selection marker to confirm the chromosomal insertion may be further included. The selection marker is to select cells transformed with the vector, that is, to confirm insertion of the desired nucleotide molecule, and the selection marker may include markers providing selectable phenotypes, such as drug resistance, auxotrophy, resistance to cytotoxic agents, or expression of surface-modified proteins. Since only cells expressing the selection marker are able to survive or to show different phenotypes under the environment treated with a selective agent, the transformed cells may be selected.

As still another aspect of the present disclosure, the present disclosure provides a microorganism producing tagatose, the microorganism including the variant protein or the polynucleotide encoding the variant protein. Specifically, the microorganism including the variant protein and/or the polynucleotide encoding the variant protein may be a microorganism prepared by transforming with the vector including the polynucleotide encoding the variant protein, but is not limited thereto.

As used herein, the term "transformation" means introduction of a vector including a polynucleotide encoding a target protein into a host cell in such a way that the protein encoded by the polynucleotide is expressed in the host cell. As long as the transformed polynucleotide may be expressed in the host cell, it may be integrated into and placed in the chromosome of the host cell, or it may exist extrachromosomally, or irrespective thereof. Further, the polynucleotide includes DNA and RNA encoding the target protein. The polynucleotide may be introduced in any form, as long as it may be introduced into the host cell and expressed therein. For example, the polynucleotide may be introduced into the host cell in the form of an expression cassette, which is a gene construct including all elements required for its autonomous expression. Commonly, the expression cassette includes a promoter operably linked to the polynucleotide, transcriptional termination signals, ribosome binding sites, and translation termination signals. The expression cassette may be in the form of a self-replicable expression vector. Also, the polynucleotide as it is may be introduced into the host cell and operably linked to sequences required for expression in the host cell, but is not limited thereto.

As used herein, the term "operably linked" means a functional linkage between a promoter sequence which initiates and mediates transcription of the polynucleotide encoding the target variant protein of the present disclosure and the polynucleotide sequence.

Still another aspect of the present disclosure provides a microorganism including the fructose-4-epimerase variant, the polynucleotide encoding the fructose-4-epimerase variant, or the vector including the polynucleotide.

The microorganism may be a microorganism producing the fructose-4-epimerase variant or tagatose.

As used herein, the term "microorganism including the fructose-4-epimerase variant" may refers to a recombinant microorganism to express the fructose-4-epimerase variant of the present disclosure. For example, the microorganism refers to a host cell or a microorganism which is able to express the variant by including the polynucleotide encoding the fructose-4-epimerase variant or by transforming with the vector including the polynucleotide encoding the fructose-4-epimerase variant. With respect to the objects of the present disclosure, the microorganism is specifically a microorganism expressing the fructose-4-epimerase variant including one or more amino acid substitutions in the amino acid sequence of SEQ ID NO: 1, and the microorganism may be a microorganism expressing the variant protein having the fructose-4-epimerase activity, wherein the amino acid substitution is substitution of one or more amino acids at one or more positions from the N-terminus, but is not limited thereto.

The fructose-4-epimerase variant of the present disclosure may be obtained by transforming a microorganism such as *E. coli* with DNA expressing the enzyme of the present disclosure or the variant thereof, culturing the microorganism to obtain a culture, disrupting the culture, and then performing purification using a column, etc. The microorganism for transformation may include *Corynebacterium glutamicum*, *Aspergillus oryzae*, or *Bacillus subtilis*, in addition to *Escherichia coli*, but is not limited thereto.

The microorganism of the present disclosure may include either a prokaryotic microorganism or a eukaryotic microorganism, as long as it is a microorganism capable of producing the fructose-4-epimerase of the present disclosure by including the nucleic acid of the present disclosure or the recombinant vector of the present disclosure. For example, the microorganism may include microorganism strains belonging to the genus *Escherichia*, the genus *Erwinia*, the genus *Serratia*, the genus *Providencia*, the genus *Corynebacterium*, and the genus *Brevibacterium*, but is not limited thereto.

The microorganism of the present disclosure may include any microorganism capable of expressing the fructose-4-epimerase of the present disclosure by various known methods, in addition to introduction of the nucleic acid or the vector.

The culture of the microorganism of the present disclosure may be produced by culturing, in a medium, the microorganism capable of expressing the fructose-4-epimerase of the present disclosure.

In the method, the "culturing" means that the microorganism is allowed to grow under appropriately controlled environmental conditions. The step of culturing the microorganism may be, but is not particularly limited to, carried out by a known batch culture method, continuous culture method, or fed batch culture method. With regard to the culture conditions, a proper pH (e.g., pH 5 to 9, specifically pH 6 to 8, and most specifically pH 6.8) may be adjusted using a basic compound (e.g., sodium hydroxide, potassium hydroxide, or ammonia) or an acidic compound (e.g., phosphoric acid or sulfuric acid), but is not particularly limited thereto. Oxygen or an oxygen-containing gas mixture may be injected into the culture to maintain aerobic conditions. The culture temperature may be maintained from 20° C. to 45° C., and specifically, from 25° C. to 40° C. for about 10 hours to about 160 hours, but is not limited thereto.

Furthermore, the culture medium to be used may include, as carbon sources, sugars and carbohydrates (e.g., glucose, sucrose, lactose, fructose, maltose, molasses, starch, and cellulose), oil and fat (e.g., soybean oil, sunflower seed oil, peanut oil, and coconut oil), fatty acids (e.g., palmitic acid, stearic acid, and linoleic acid), alcohols (e.g., glycerol and ethanol), and organic acids (e.g., acetic acid) individually or in combination, but is not limited thereto. As nitrogen sources, nitrogen-containing organic compounds (e.g., peptone, yeast extract, meat broth, malt extract, corn steep liquor, soybean meal, and urea), or inorganic compounds (e.g., ammonium sulfate, ammonium chloride, ammonium phosphate, ammonium carbonate, and ammonium nitrate) may be used individually or in combination, but are not limited thereto. As phosphorus sources, dipotassium hydrogen phosphate, potassium dihydrogen phosphate, and corresponding sodium salts thereof may be used individually or in combination, but are not limited thereto. Further, the medium may include essential growth-stimulating substances including other metal salts (e.g., magnesium sulfate or iron sulfate), amino acids, and vitamins.

Still another aspect of the present disclosure provides a composition for producing tagatose, the composition including the fructose-4-epimerase including the amino acid sequence of SEQ ID NO: 1 or the fructose-4-epimerase variant; the microorganism including the same; or the culture of the microorganism.

The composition for producing tagatose of the present disclosure may further include fructose.

In addition, the composition for producing tagatose of the present disclosure may further include any appropriate excipient commonly used in the corresponding composition for producing tagatose. The excipient may include, for example, a preservative, a wetting agent, a dispersing agent, a suspending agent, a buffer, a stabilizer, an isotonic agent, etc., but is not limited thereto.

The composition for producing tagatose of the present disclosure may further include a metal ion or a metal salt. In a specific embodiment, a metal of the metal ion or the metal salt may be a metal containing a divalent cation. Specifically, the metal of the present disclosure may be nickel (Ni), iron (Fe), cobalt (Co), magnesium (Mg), or manganese (Mn). More specifically, the metal salt may be $MgSO_4$, $FeSO_4$, $NiSO_4$, $NiCl_2$, $CoSO_4$, $MgCl_2$, $MnCl_2$, or $MnSO_4$.

Still another aspect of the present disclosure provides a method of preparing tagatose, the method including the step of converting fructose into tagatose by contacting fructose with the microorganism including the fructose-4-epimerase including the amino acid sequence of SEQ ID NO: 1 or the fructose-4-epimerase variant; or the culture thereof.

For example, the contacting of the present disclosure may be performed under a condition of pH 5.0 to pH 9.0, a temperature condition of 30° C. to 80° C., and/or for 0.5 hr to 48 hr.

Specifically, the contacting of the present disclosure may be performed under a condition of pH 6.0 to pH 9.0 or pH 7.0 to pH 9.0. Further, the contacting of the present disclosure may be performed under a temperature condition of 35° C. to 80° C., 40° C. to 80° C., 45° C. to 80° C., 50° C. to 80° C., 55° C. to 80° C., 60° C. to 80° C., 30° C. to 70° C., 35° C. to 70° C., 40° C. to 70° C., 45° C. to 70° C., 50° C. to 70° C., 55° C. to 70° C., 60° C. to 70° C., 30° C. to 65° C., 35° C. to 65° C., 40° C. to 65° C., 45° C. to 65° C., 50° C. to 65° C., 55° C. to 65° C., 30° C. to 60° C., 35° C. to 60° C., 40° C. to 60° C., 45° C. to 60° C., 50° C. to 60° C. or 55° C. to 60° C. Further, the contacting of the present disclosure may be performed for 0.5 hr to 36 hr, 0.5 hr to 24 hr, 0.5 hr to 12 hr, 0.5 hr to 6 hr, 1 hr, to 48 hr, 1 hr to 36 hr, 1 hr to 24 hr, 1 hr to 12 hr, 1 hr to 6 hr, 3 hr to 48 hr, 3 hr to 36 hr, 3 hr to 24 hr, 3 hr to 12 hr, 3 hr to 6 hr, 6 hr to 48 hr, 6 hr to 36 hr, 6 hr to 24 hr, 6 hr to 12 hr, 12 hr to 48 hr, 12 hr to 36 hr, 12 hr to 24 hr, 18 hr, to 48 hr, 18 hr to 36 hr, or 18 hr to 30 hr.

Further, the contacting of the present disclosure may be performed in the presence of a metal ion or a metal salt. The applicable metal ion or metal salt is the same as described above.

The production method of the present disclosure may further include the step of separating and/or purifying the produced tagatose. The separation and/or purification may be performed using a method commonly used in the art. Non-limiting examples may include dialysis, precipitation, adsorption, electrophoresis, ion exchange chromatography, fractional crystallization, etc. The purification may be performed only by a single method or by two or more methods in combination.

In addition, the production method of the present disclosure may further include the step of performing decolorization and/or deionization, before or after the separation and/or purification step(s). By performing the decolorization and/or deionization, it is possible to obtain tagatose with higher quality.

For another example, the production method of the present disclosure may further include the step of performing crystallization of tagatose, after the step of converting into tagatose of the present disclosure, performing the separation and/or purification, or performing the decolorization and/or deionization. The crystallization may be performed by a crystallization method commonly used. For example, the crystallization may be performed by cooling crystallization.

Further, the production method of the present disclosure may further include the step of concentrating tagatose, before the step of performing crystallization. The concentrating may increase the crystallization efficiency.

For another example, the production method of the present disclosure may further include the step of contacting unreacted fructose with the enzyme of the present disclosure, the microorganism expressing the enzyme, or the culture of the microorganism after the step of separation and/or purification, or the step of reusing a crystal-separated mother solution in the step of separation and/or purification after the step of performing the crystallization of the present disclosure, or a combination thereof. The additional steps are economically advantageous in that tagatose may be obtained with higher yield and the amount of fructose to be discarded may be reduced.

MODE FOR INVENTION

Hereinafter, the present disclosure will be described in more detail with reference to Examples. However, these Examples are for the purpose of illustrating the present disclosure, and the scope of the present disclosure is not intended to be limited by these Examples. It will be apparent to those skilled in the art to which the present disclosure pertains.

Example 1. Preparation of Recombinant Expression Vectors and Transformants, Each Including Fructose-4-Epimerase Gene Example 1-1. Preparation of Wild-Type Fructose-4-Epimerase To prepare fructose-4-epimerase, *Kosmotoga olearia*-derived amino acid sequence (SEQ ID NO: 1) and genetic information were obtained to prepare a vector expressible in *E. coli* and a transformed microorganism (transformant). It was confirmed that the sequence may be used as a fructose-4-epimerase to convert fructose into tagatose (FIG. 1).

In detail, a nucleotide sequence of tagatose-bisphosphate aldolase was selected from nucleotide sequences of *Kosmotoga olearia*, which is registered in KEGG (Kyoto Encyclopedia of Genes and Genomes). Based on information of an amino acid sequence (SEQ ID NO: 1) of tagatose-bisphosphate aldolase class II accessory protein AgaZ of *Kosmotoga olearia* and a nucleotide sequence thereof (SEQ ID NO: 2), it was inserted into pBT7-C-His which is a vector expressible in *E. coli* to synthesize and prepare a recombinant expression vector pBT7-C-His-KO, performed by Bioneer Corp.

To induce protein expression, the vector was transformed into an *E. coli* expression strain BL21(DE3), and the resulting product was designated as *E. coli* BL21(DE3)/CJ_KO_F4E. *E. coli* BL21(DE3)/CJ_KO_F4E was deposited on Mar. 24, 2017 under the provisions of the Budapest Treaty with Accession No. KCCM11999P.

To prepare a recombinant enzyme, the *E. coli* BL21 (DE3)/CJ_KO_F4E was seeded in a culture tube containing 5 mL of an LB liquid medium supplemented with an ampicillin antibiotic, and seed-cultured in a shaking incubator at 37° C. until absorbance at 600 nm reached 2.0. The culture broth obtained from the seed culture was seeded in a culture flask containing a liquid medium containing LB and lactose which is a protein expression regulator, followed by main culture. During the culturing process, a shaking speed was 180 rpm and a culturing temperature was maintained at 37° C. The culture broth was centrifuged at 8,000 rpm 4° C. for 20 minutes, and then the microorganism was recovered. The recovered microorganism was washed with a 50 mM Tris-HCl (pH 8.0) buffer solution twice, and resuspended in a 50 mM $NaH_2PO_4$ (pH 8.0) buffer solution containing 10 mM imidazole and 300 mM NaCl. The resuspended microorganism was disrupted using a sonicator, and centrifuged at 13,000 rpm and 4° C. for 20 minutes to collect only the supernatant. The supernatant was purified using His-taq affinity chromatography, and a 50 mM $NaH_2PO_4$ (pH 8.0) buffer solution containing 20 mM imidazole and 300 mM NaCl was applied in a 10-fold volume of a filler to remove non-specific binding proteins. Finally, 50 mM $NaH_2PO_4$ (pH 8.0) buffer solution containing 250 mM imidazole and 300 mM NaCl was applied to perform elution and purification. Then, dialysis was performed using a 50 mM Tris-HCl (pH 8.0) buffer solution, and the enzyme was obtained for characterization of the enzyme.

Example 1-2. Evaluation of Conversion Activity of Tagatose from Fructose

To measure activity of the enzyme obtained in Example 1-1, 30% by weight of fructose was used, to which 50 mM Tris-HCl (pH 8.0), 1 mM $CoSO_4$, and 20 mg/ml of pure enzyme isolated in Example 2 were added, and allowed to react at 60° C. for 2 hours. A concentration of tagatose converted by CJ_KO_F4E and a conversation rate of tagatose from fructose was 16.0%.

The conversion rate was calculated by the following equation: conversion rate=tagatose weight/initial fructose weight×100

Example 2. Preparation of Variant Library and Screening of Activity-Improved Variant Using Library Error-prone PCR was performed using *Kosmotoga olearia*-derived fructose-4-epimerase gene in Example 1 as a template to construct a fructose-4-epimerase variant library. In detail, random mutation was induced using a diversify random mutagenesis kit (ClonTech) to generate 2 to 3 variations per 1000 base pairs in the fructose-4-epimerase gene. PCR reaction conditions are shown in the following Tables 1 and 2. The gene library encoding the fructose-4-epimerase variant was constructed and inserted into *E. coli* BL21(DE3).

TABLE 1

| Composition of reaction solution | Addition amount (μl) |
| --- | --- |
| PCR Grade Water | 36 |
| 10X TITANIUM Taq Buffer | 5 |
| MnSO4 (8 mM) | 4 |

TABLE 1-continued

| Composition of reaction solution | Addition amount (μl) |
|---|---|
| dGTP (2 mM) | 1 |
| 50X Diversify dNTP Mix | 1 |
| Primer mix | 1 |
| Template DNA | 1 |
| TITANIUM Taq Polym. | 1 |

TABLE 2

| Step | Temperature (° C.) | Time (sec) | Cycle |
|---|---|---|---|
| Initial Denaturation | 94 | 30 | 1 |
| Denaturation | 94 | 30 | 25 |
| Annealing/Extension | 68 | 60 | |
| Final Extension | 68 | 60 | 1 |

E. coli BL21(DE3) having the pBT7-C-His plasmid harboring the fructose-4-epimerase variant gene was seeded in a deep well rack containing 0.2 mL of an LB liquid medium supplemented with an ampicillin antibiotic, and seed-cultured in a shaking incubator at 37° C. for 16 hours or longer. The culture broth obtained from the seed culture was seeded in a culture deep well rack containing a liquid medium containing LB and lactose which is a protein expression regulator, followed by main culture. The seed culture and main culture were performed under conditions of a shaking speed of 180 rpm and 37° C. Next, the culture broth was centrifuged at 4,000 rpm and 4° C. for 20 minutes, and then the microorganism was recovered.

For high-speed screening of a large amount of the activity-improved variant enzyme from the prepared random mutation library, a colorimetric method capable of specifically quantifying D-fructose was used. In detail, a 70% folin-ciocalteu reagent (SIGMA-ALDRICH) and a substrate reaction solution were mixed at a ratio of 15:1, and allowed to react at 80° C. for 5 minutes. OD values were measured at 900 nm and used for comparative analysis.

The reaction solutions (substrate D-fructose) were analyzed by using the microorganism samples having the wild-type enzyme and the activity-improved enzyme. As a result, it was evaluated that the colorimetric method was effective, and the prepared library was used for screening of improved activity.

The library was used in screening of the activity-improved variants. In detail, variants having the activity (conversion of D-fructose into D-tagatose) by comparing the relative activity thereof with that of the wild-type enzyme (SEQ ID NO: 1) were selected. The sequencing analysis of the corresponding genes was performed, and then information of amino acid variations was analyzed.

Among them, 50 colonies having the highest activity were selected, and sequenced to examine their base sequences. As a result, variations were found in a total of 47 sites, specifically, at positions 8, 20, 23, 25, 26, 29, 45, 51, 53, 63, 86, 91, 97, 110, 133, 144, 146, 151, 155, 167, 172, 173, 174, 181, 191, 239, 263, 266, 285, 294, 298, 308, 315, 316, 317, 323, 336, 347, 359, 367, 385, 386, 388, 389, 410, 414, and 417.

Example 3. Preparation of Additional Characteristic-Improved Enzymes and Selection of Variant Enzymes Information of the improved sites as selected above was incorporated to prepare variant enzymes, and variant enzymes having improved unit activity of the fructose-4-epimerization conversion reaction were developed.

Example 3-1. Saturation Mutagenesis

The recombinant expression vector pBT7-C-His-KO which was prepared for expressing the wild-type enzyme gene in E. coli BL21(DE3) (expressing the recombinant enzyme having 6×His-tag at the C-terminus of the wild-type) was used as a template for saturation mutagenesis for the construction of a variant library in which 47 activity-improved sites selected in Example 2 were added. In view of mutation frequency variation and variant yield, etc., inversed PCR-based saturation mutagenesis was used (2014. Anal. Biochem. 449:90-98), and in order to minimize screening scales of the constructed variant library (minimize the number of codons introduced for saturation mutagenesis), a mixed primer NDT/VMA/ATG/TGG (2012. Biotechniques 52:149-158) in which stop codons were excluded and rare codons for E. coli were minimized was designed and used. In detail, a primer having a total length of 33 bp was constructed using 15 bp residing at the front side, 3 bp to be substituted, and 15 bp residing at the rear side of each site. PCR was performed by repeating 30 cycles consisting of denaturing at 94° C. for 2 minutes, denaturing at 94° C. from 30 seconds, annealing at 60° C. for 30 seconds, and extending at 72° C. for 10 minutes, followed by elongation at 72° C. for 60 minutes. After construction of a saturation mutagenesis library for the selected amino acid sites, variants for each library were randomly selected (<11 variations). Base sequences were analyzed to evaluate amino acid mutation frequency. Based on the analysis results, scales of screening each library were set with sequence coverage of 90% or more (2003. Nucleic Acids Res. 15; 31:e30).

Through the saturation mutagenesis of 47 single sites, variant candidates retaining high activity were prepared, and sequencing analysis was performed to examine the variation sites. Thus, a total of 288 variants were obtained (Table 3).

TABLE 3

| Variation site | Existing sequence | Mutated sequence |
|---|---|---|
| 8 | D | A, E, H, L, P, Q, V, |
| 20 | C | R |
| 23 | S | C |
| 25 | C | A, V, S, D, H, F, L, G, N, M, E, Q, P, K, Y, R, W, I, T |
| 26 | S | A, T, V |
| 29 | R | W, C, K, E, Q, A, S, V, L, P |
| 45 | T | A, Q, V, K, E, M |
| 51 | T | V, P, I, N, F, D, H, W, Q, E, L, A, G, C, M, K, Y, S, R |
| 53 | N | W, F, C, K, R, G, S, L, T, P |
| 63 | G | P, A, M, V, E, L |
| 86 | K | R, V, A, M, L, G |
| 91 | G | F, W, Y |
| 97 | N | K, L, E, Y, P |
| 110 | N | Y |
| 133 | R | P, N, E, V, Q, L |
| 144 | P | A, I, V, F, S |
| 146 | N | L, P, H, G |
| 151 | A | G |
| 155 | A | G |
| 167 | E | V, R, A, G, T, L, D |
| 172 | L | T, A |
| 173 | R | A, T, E, V, D |
| 174 | P | K, G, L, R, D, M, V, F, S, Y, W |
| 181 | D | I, A, L, K, R, P, G, M |
| 191 | E | T, R, G, V, S, L, I, A |
| 239 | N | V, G, A, E, K, W, L, P |

TABLE 3-continued

| Variation site | Existing sequence | Mutated sequence |
|---|---|---|
| 263 | I | A, Q, L, K, E |
| 266 | E | L, R, W, D, G, A, T, P, C, V, Y, I |
| 285 | G | M, V, E, H, D, Q, Y, L |
| 294 | A | G |
| 298 | A | G |
| 308 | S | V, A, D, I, H, L, R, W |
| 315 | Y | D, V, A, P, H, L |
| 316 | D | L, V, N, K, P, R, M, T |
| 317 | T | V, I, D, H, R, S |
| 323 | N | M, K, G, V, L, H, D, I, R |
| 336 | P | A, R, G |
| 347 | E | D, G, N, P, S |
| 359 | L | V, R, G, A, D, N, T |
| 367 | N | A, G, L, R, I, V |
| 385 | K | R, A |
| 386 | E | T, I, V, A, L, D, H, S |
| 388 | P | V, D, S, R, I, G, T |
| 389 | L | K, G, R, V, D, S, E, M |
| 410 | K | V, L, A, T |
| 414 | S | P, Q |
| 417 | K | G, V, S, P, R, D, L, A, M |

Example 3-2. Preparation of Variant Enzymes

In order to evaluate relative activity of fructose-4-epimerization for a variant enzyme at a single site with improved unit activity and a variant enzyme at multiple sites with combination thereof, the saturation mutagenesis library gene prepared in 3-1 was transformed into E. coli BL21 (DE3), and each transformed microorganism was seeded in a culture tube containing 5 mL of LB liquid medium containing an ampicillin antibiotic, and seed-cultured in a shaking incubator at 37° C. until absorbance at 600 nm reached 2.0. The culture broth obtained from the seed culture was seeded in a culture flask containing a liquid medium containing LB and lactose which is a protein expression regulator, followed by main culture. The seed culture and main culture were performed under conditions of a shaking speed of 180 rpm and 37° C. Next, the culture broth was centrifuged at 8,000 rpm and 4° C. for 20 minutes, and then the microorganism was recovered. The recovered microorganism was washed with a 50 mM Tris-HCl (pH 8.0) buffer solution twice, and resuspended in a 50 mM NaH$_2$PO$_4$ (pH 8.0) buffer solution containing 10 mM imidazole and 300 mM NaCl. The resuspended microorganism was disrupted using a sonicator, and centrifuged at 13,000 rpm and 4° C. for 20 minutes to collect only the supernatant. The supernatant was purified using His-taq affinity chromatography, and a 50 mM NaH$_2$PO$_4$ (pH 8.0) buffer solution containing 20 mM imidazole and 300 mM NaCl was applied in a 10-fold volume of a filler to remove non-specific binding proteins. Subsequently, 50 mM NaH$_2$PO$_4$ (pH 8.0) buffer solution containing 250 mM imidazole and 300 mM NaCl was further applied to perform elution and purification. Then, dialysis was performed using a 50 mM Tris-HCl (pH 8.0) buffer solution, and the respective purified enzymes were obtained for characterization of the enzymes.

Example 4. Comparative Evaluation of Characteristics of Variant Enzymes

To measure the fructose-4-epimerization activity of the recombinant variant enzymes obtained in Example 3-2, 50 mM Tris-HCl (pH 8.0), 3 mM MnSO$_4$, and each 5 mg/mL of the enzymes was added to 30% by weight of fructose, and allowed to react at 60° C. for 2 hours.

As a result, the conversion activity of the wild-type (KO) was 4.7%, and all the variants of the present disclosure had fructose-4-epimerization activity. In particular, their activity was increased, as compared with that of the wild-type. The detailed results are shown in the following Table 4.

TABLE 4

| Variation site | Existing sequence | Mutated sequence | Relative activity (%) |
|---|---|---|---|
| 20 | C | R | 193 |
| 23 | S | C | 207 |
| 26 | S | A | 100 |
|  |  | T | 173 |
|  |  | V | 100 |
| 45 | T | A | 141 |
|  |  | Q | 185 |
|  |  | V | 179 |
|  |  | K | 197 |
|  |  | E | 203 |
|  |  | M | 241 |
| 51 | T | V | 163 |
|  |  | P | 163 |
| 53 | N | W | 141 |
|  |  | F | 188 |
|  |  | C | 108 |
|  |  | G | 163 |
|  |  | S | 200 |
|  |  | T | 238 |
|  |  | P | 217 |
| 63 | G | A | 126 |
|  |  | E | 100 |
| 86 | K | R | 147 |
|  |  | V | 127 |
|  |  | M | 297 |
|  |  | L | 161 |
|  |  | G | 111 |
| 91 | G | Y | 136 |
|  |  | W | 131 |
| 133 | R | P | 133 |
|  |  | N | 143 |
|  |  | Q | 178 |
|  |  | L | 285 |
| 144 | P | A | 108 |
|  |  | I | 113 |
|  |  | V | 117 |
|  |  | F | 248 |
|  |  | S | 222 |
| 151 | A | G | 140 |
| 172 | L | T | 142 |
|  |  | A | 120 |
| 173 | R | A | 193 |
|  |  | T | 169 |
|  |  | E | 183 |
|  |  | V | 129 |
|  |  | D | 163 |
| 174 | P | K | 239 |
|  |  | R | 132 |
|  |  | D | 171 |
|  |  | V | 130 |
|  |  | F | 130 |
| 181 | D | R | 108 |
|  |  | A | 115 |
|  |  | K | 112 |
| 191 | E | T | 159 |
|  |  | R | 140 |
|  |  | G | 129 |
|  |  | V | 175 |
|  |  | S | 152 |
|  |  | L | 187 |
|  |  | I | 179 |
|  |  | A | 159 |
| 266 | E | Y | 116 |
| 294 | A | G | 116 |
| 298 | A | G | 200 |
| 316 | D | L | 157 |
|  |  | V | 152 |

TABLE 4-continued

| Variation site | Existing sequence | Mutated sequence | Relative activity (%) |
|---|---|---|---|
| | | N | 194 |
| | | P | 193 |
| | | R | 133 |
| | | M | 137 |
| | | T | 129 |
| 317 | T | V | 122 |
| | | I | 272 |
| | | D | 136 |
| | | H | 159 |
| | | R | 182 |
| | | S | 166 |
| 323 | N | G | 190 |
| | | L | 181 |
| 336 | P | A | 107 |
| | | R | 366 |
| 347 | E | S | 106 |
| | | G | 131 |
| | | N | 134 |
| | | P | 123 |
| 359 | L | V | 153 |
| 385 | K | R | 133 |
| 386 | E | I | 175 |
| | | V | 142 |
| | | L | 134 |
| | | D | 133 |
| | | H | 137 |
| | | S | 94 |
| 388 | P | V | 120 |
| | | D | 206 |
| | | S | 219 |
| | | R | 277 |
| | | I | 205 |
| | | G | 324 |
| | | T | 120 |
| 389 | L | K | 336 |
| | | G | 282 |
| | | R | 288 |
| | | V | 212 |
| | | D | 263 |
| | | S | 222 |
| | | E | 291 |
| | | M | 261 |
| 410 | K | V | 163 |
| | | L | 223 |
| | | A | 152 |
| | | T | 130 |
| 414 | S | P | 142 |
| | | Q | 250 |
| KO | | | 100 |

The above results showed that the variants of the present disclosure had increased fructose-4-epimerization activity, as compared with the wild-type.

Example 5. Preparation of Variant Enzymes and Selection of Activity, Stability-Improved Variant Enzymes Genes and enzymes of single-site saturation mutagenesis of 15 target sites (at positions 8, 25, 29, 97, 110, 146, 155, 167, 239, 263, 285, 308, 315, 367, and 417) obtained in Example 3-2 were prepared.

Example 5-1. Saturation Mutagenesis

The recombinant expression vector pBT7-C-His-KO which was prepared for expressing the wild-type enzyme gene in *E. coli* BL21(DE3) (expressing the recombinant enzyme having 6×His-tag at the C-terminus of the wild-type) was used as a template for saturation mutagenesis for variant library construction. In view of mutation frequency variation and variant yield, etc., inversed PCR-based saturation mutagenesis was used (2014. Anal. Biochem. 449: 90-98), and in order to minimize screening scales of the constructed variant library (minimize the number of codons introduced for saturation mutagenesis), a mixed primer NDT/VMA/ATG/TGG (2012. Biotechniques 52:149-158) in which stop codons were excluded and rare codons for *E. coli* were minimized was designed and used. In detail, a primer having a total length of 33 bp was constructed using 15 bp residing at the front side, 3 bp to be substituted, and 15 bp residing at the rear side of each site. PCR was performed by repeating 30 cycles consisting of denaturing at 94° C. for 2 minutes, denaturing at 94° C. from 30 seconds, annealing at 60° C. for 30 seconds, and extending at 72° C. for 10 minutes, followed by elongation at 72° C. for 60 minutes. After construction of a saturation mutagenesis library for the selected amino acid sites, variants for each library were randomly selected (<11 variations). Base sequences were analyzed to evaluate amino acid mutation frequency (Table 5). Based on the analysis results, scales of screening each library were set with sequence coverage of 90% or more (2003. Nucleic Acids Res. 15; 31:e30).

TABLE 5

| Variation site | | | | | | | | | | | | | | | |
|---|---|---|---|---|---|---|---|---|---|---|---|---|---|---|---|
| D8 | A | E | H | L | P | Q | V | P | | | | | | | |
| C25 | A | V | S | D | H | F | L | G | N | M | E | Q | P | K | Y | R | W | I | T |
| R29 | W | C | K | E | Q | A | S | V | L | P | | | | | |
| N97 | K | L | E | Y | P | | | | | | | | | | |
| N110 | Y | | | | | | | | | | | | | | |
| N146 | L | P | H | G | | | | | | | | | | | |
| A155 | G | | | | | | | | | | | | | | |
| E167 | V | R | A | G | T | D | | | | | | | | | |
| N239 | V | G | A | E | K | W | L | P | | | | | | | |
| I263 | A | Q | L | K | E | | | | | | | | | | |
| G285 | M | V | E | H | D | Q | Y | L | | | | | | | |
| S308 | V | A | D | I | V | H | L | R | W | | | | | | |
| Y315 | D | V | A | P | H | L | | | | | | | | | |
| N367 | A | G | L | R | I | V | | | | | | | | | |
| K417 | G | V | S | P | R | D | L | A | A | M | P | | | | |

Example 5-2. Preparation of Activity and Thermal Stability-Improved Variant Enzymes In order to evaluate relative activity of fructose-4-epimerization for a variant enzyme at a single site with improved unit activity and thermal stability and a variant enzyme at multiple sites with combination thereof, the saturation mutagenesis library gene prepared in 2-1 was transformed into *E. coli* BL21(DE3), and each transformed microorganism was seeded in a culture tube containing 5 mL of LB liquid medium containing an ampicillin antibiotic, and seed-cultured in a shaking incubator at 37° C. until absorbance at 600 nm reached 2.0. The culture broth obtained from the seed culture was seeded in a culture flask containing a liquid medium containing LB and lactose which is a protein expression regulator, followed by main culture. The seed culture and main culture were performed under conditions of a shaking speed of 180 rpm and 37° C. Next, the culture broth was centrifuged at 8,000 rpm and 4° C. for 20 minutes, and then the microorganism was recovered. The recovered microorganism was washed with a 50 mM Tris-HCl (pH 8.0) buffer solution twice, and resuspended in a 50 mM $NaH_2PO_4$ (pH 8.0) buffer solution containing 10 mM imidazole and 300 mM NaCl. The resuspended microorganism was disrupted using a sonicator, and centrifuged at 13,000 rpm and 4° C. for 20 minutes to collect only the supernatant. The supernatant was purified using His-taq affinity chromatography, and a 50 mM $NaH_2PO_4$ (pH 8.0) buffer solution containing 20 mM imidazole and 300 mM NaCl was applied in a 10-fold volume of a filler to remove non-specific binding proteins. Subsequently, 50 mM $NaH_2PO_4$ (pH 8.0) buffer solution containing 250 mM imidazole and 300 mM NaCl was further applied to perform elution and purification. Then, dialysis was performed using a 50 mM Tris-HCl (pH 8.0) buffer solution, and the respective purified enzymes were obtained for characterization of the enzymes.

Example 6. Comparative Evaluation of Characteristics of Activity, Stability-Improved Variant Enzymes To measure the fructose-4-epimerization activity of the recombinant variant enzymes obtained in Example 5-2, 50 mM Tris-HCl (pH 8.0), 3 mM $MnSO_4$, and each 5 mg/mL of the enzymes was added to 30% by weight of fructose, and allowed to react at 60° C. for 2 hours. Furthermore, to measure the fructose-4-epimerization stability of the obtained recombinant variant enzymes, each 5 mg/mL of the enzymes was left at 60° C. for at least 19 hours and up to 90 hours, and then left on ice for 5 minutes. 50 mM Tris-HCl (pH 8.0) and 3 mM $MnSO_4$ were added to 30% by weight of fructose, which was allowed to react.

As a result, all the variants of the present disclosure had increased fructose-4-epimerization conversion activity and stability, as compared with those of the wild-type. The detailed results of the activity are shown in the following Table 6, and the detailed results of the stability are shown in FIGS. 2 and 3.

TABLE 6

| Variation site | Existing sequence | Mutated sequence | Relative activity (%) |
|---|---|---|---|
| 8 | D | A | 360 |
|   |   | E | 357 |
|   |   | H | 379 |
|   |   | L | 364 |
|   |   | P | 484 |
|   |   | Q | 340 |
|   |   | V | 263 |
| 25 | C | A | 152 |
|   |   | V | 142 |
|   |   | S | 165 |
| 29 | R | W | 399 |
|   |   | C | 330 |
|   |   | K | 273 |
|   |   | E | 264 |
|   |   | Q | 279 |
|   |   | A | 267 |
|   |   | S | 383 |
|   |   | V | 333 |
|   |   | L | 331 |
|   |   | P | 287 |
| 97 | N | K | 110 |
|   |   | L | 458 |
|   |   | E | 165 |
|   |   | Y | 528 |
|   |   | P | 110 |
| 110 | N | Y | 303 |
| 146 | N | L | 433 |
|   |   | P | 439 |
|   |   | H | 461 |
|   |   | G | 456 |
| 155 | A | G | 156 |
| 167 | E | V | 261 |
|   |   | R | 253 |
|   |   | A | 346 |
|   |   | G | 322 |
|   |   | T | 193 |
|   |   | D | 490 |
| 239 | N | V | 112 |
|   |   | G | 242 |
|   |   | A | 226 |
|   |   | E | 132 |
|   |   | K | 215 |
|   |   | W | 102 |
|   |   | L | 169 |
|   |   | P | 139 |
| 263 | I | A | 289 |
|   |   | Q | 328 |
|   |   | L | 211 |
|   |   | K | 244 |
|   |   | E | 189 |
| 285 | G | M | 170 |
|   |   | V | 170 |
|   |   | E | 141 |
|   |   | H | 304 |
|   |   | D | 259 |
|   |   | Q | 181 |
|   |   | Y | 204 |
|   |   | L | 200 |
| 308 | S | V | 211 |
|   |   | A | 172 |
|   |   | D | 206 |
|   |   | I | 206 |
|   |   | H | 206 |
|   |   | L | 222 |
|   |   | R | 211 |
|   |   | W | 228 |
| 315 | Y | D | 137 |
|   |   | V | 133 |
|   |   | A | 149 |
|   |   | P | 153 |
|   |   | H | 137 |
|   |   | L | 133 |
| 367 | N | A | 234 |
|   |   | G | 285 |
|   |   | L | 238 |
|   |   | R | 255 |
|   |   | I | 300 |
|   |   | V | 234 |

TABLE 6-continued

| Variation site | Existing sequence | Mutated sequence | Relative activity (%) |
|---|---|---|---|
| 417 | K | G | 236 |
| | | V | 274 |
| | | S | 309 |
| | | P | 258 |
| | | R | 244 |
| | | D | 287 |
| | | L | 288 |
| | | A | 321 |
| | | M | 206 |
| | | P | 236 |
| KO(WT) | | | 100 |

The present inventors transformed into E. coli BL21 (DE3) strain to prepare transformants (transformed microorganisms) designated as E. coli BL21(DE3)/CJ_KO_F4E_M1(C25S), E. coli BL21(DE3)/CJ_KO_F4E_M2(T51V), E. coli BL21(DE3)/CJ_KO_F4E_M5(T317Y), respectively and deposited the transformants on Sep. 19, 2018 at the Korean Culture Center of Microorganisms (KCCM) which is an International Depositary Authority under the provisions of the Budapest Treaty with Accession Nos. KCCM12320P (E. coli BL21 (DE3)/CJ_KO_F4E_M1), KCCM12321P (E. coli BL21 (DE3)/CJ_KO_F4E_M2), KCCM12324P (E. coli BL21 (DE3)/CJ_KO_F4E_M5), respectively.

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A fructose-4-epimerase variant comprising the amino acid sequence of SEQ ID NO:1 with one or more amino acid substitutions, wherein the variant includes an amino acid sequence having at least 90% sequence identity to the amino acid sequence of SEQ ID NO: 1, wherein the one or more amino acid substitutions are selected from the group consisting of amino acids at positions of 8, 20, 23, 25, 26, 29, 45, 51, 53, 63, 86, 91, 97, 110, 133, 144, 146, 151, 155, 167, 172, 173, 174, 181, 191, 239, 263, 266, 285, 294, 298, 308, 315, 316, 317, 323, 336, 347, 359, 367, 385, 386, 388, 389, 410, 414, and 417 in the amino acid sequence of SEQ ID NO: 1.

2. The fructose-4-epimerase variant of claim 1, wherein the one or more amino acid substitutions comprise substituting with an amino acid selected from the group consisting of glycine, alanine, arginine, valine, leucine, methionine, isoleucine, threonine, asparagine, glutamine, proline, serine, tryptophan, phenylalanine, histidine, cysteine, tyrosine, lysine, aspartic acid, and glutamic acid.

3. A composition for producing tagatose, the composition comprising the fructose-4-epimerase variant of claim 1.

4. The composition for producing tagatose of claim 3, the composition further comprising fructose.

5. A method of preparing tagatose, the method comprising the step of converting fructose into tagatose by contacting fructose with fructose-4-epimerase comprising the amino acid sequence of SEQ ID NO: 1 or the fructose-4-epimerase variant of claim 1.

6. A composition for producing tagatose, the composition comprising the fructose-4-epimerase variant of claim 2.

7. The composition for producing tagatose of claim 6, the composition further comprising fructose.

8. A method of preparing tagatose, the method comprising the step of converting fructose into tagatose by contacting fructose with the fructose-4-epimerase variant of claim 2.

* * * * *

SEQUENCE LISTING

```
<160> NUMBER OF SEQ ID NOS: 24

<210> SEQ ID NO 1
<211> LENGTH: 435
<212> TYPE: PRT
<213> ORGANISM: Unknown
<220> FEATURE:
<223> OTHER INFORMATION: Kosmotoga olearia
<220> FEATURE:
<221> NAME/KEY: PEPTIDE
<222> LOCATION: (1)..(435)
<223> OTHER INFORMATION: Tagatose-bisphosphate aldolase

<400> SEQUENCE: 1

Met Lys Lys His Pro Leu Gln Asp Ile Val Ser Leu Gln Lys Gln Gly
1               5                   10                  15

Ile Pro Lys Gly Val Phe Ser Val Cys Ser Ala Asn Arg Phe Val Ile
            20                  25                  30

Glu Thr Thr Leu Glu Tyr Ala Lys Met Lys Gly Thr Thr Val Leu Ile
        35                  40                  45

Glu Ala Thr Cys Asn Gln Val Asn Gln Phe Gly Gly Tyr Thr Gly Met
    50                  55                  60

Thr Pro Ala Asp Phe Arg Glu Met Val Phe Ser Ile Ala Glu Asp Ile
65                  70                  75                  80

Gly Leu Pro Lys Asn Lys Ile Ile Leu Gly Gly Asp His Leu Gly Pro
                85                  90                  95

Asn Pro Trp Lys Gly Gln Pro Ser Asp Gln Ala Met Arg Asn Ala Ile
            100                 105                 110

Glu Met Ile Arg Glu Tyr Ala Lys Ala Gly Phe Thr Lys Leu His Leu
        115                 120                 125

Asp Ala Ser Met Arg Leu Ala Asp Pro Gly Asn Glu Asn Glu Pro
    130                 135                 140

Leu Asn Pro Glu Val Ile Ala Glu Arg Thr Ala Leu Leu Cys Leu Glu
145                 150                 155                 160

Ala Glu Arg Ala Phe Lys Glu Ser Ala Gly Ser Leu Arg Pro Val Tyr
                165                 170                 175

Val Ile Gly Thr Asp Val Pro Pro Gly Gly Ala Gln Asn Glu Gly
            180                 185                 190

Lys Ser Ile His Val Thr Ser Val Gln Asp Phe Glu Arg Thr Val Glu
        195                 200                 205
```

Leu Thr Lys Lys Ala Phe Phe Asp His Gly Leu Tyr Glu Ala Trp Gly
            210                 215                 220

Arg Val Ile Ala Val Val Gln Pro Gly Val Glu Phe Gly Asn Glu
225                 230                 235                 240

His Ile Phe Glu Tyr Asp Arg Asn Arg Ala Arg Glu Leu Thr Glu Ala
                245                 250                 255

Ile Lys Lys His Pro Asn Ile Val Phe Glu Gly His Ser Thr Asp Tyr
            260                 265                 270

Gln Thr Ala Lys Ala Leu Lys Glu Met Val Glu Asp Gly Val Ala Ile
        275                 280                 285

Leu Lys Val Gly Pro Ala Leu Thr Phe Ala Leu Arg Glu Ala Phe Phe
290                 295                 300

Ala Leu Ser Ser Ile Glu Lys Glu Leu Phe Tyr Asp Thr Pro Gly Leu
305                 310                 315                 320

Cys Ser Asn Phe Val Glu Val Val Glu Arg Ala Met Leu Asp Asn Pro
                325                 330                 335

Lys His Trp Glu Lys Tyr Tyr Gln Gly Glu Arg Glu Asn Arg Leu
            340                 345                 350

Ala Arg Lys Tyr Ser Phe Leu Asp Arg Leu Arg Tyr Tyr Trp Asn Leu
        355                 360                 365

Pro Glu Val Arg Thr Ala Val Asn Lys Leu Ile Thr Asn Leu Glu Thr
370                 375                 380

Lys Glu Ile Pro Leu Thr Leu Ile Ser Gln Phe Met Pro Met Gln Tyr
385                 390                 395                 400

Gln Lys Ile Arg Asn Gly Leu Leu Arg Lys Asp Pro Ile Ser Leu Ile
                405                 410                 415

Lys Asp Arg Ile Thr Leu Val Leu Asp Asp Tyr Tyr Phe Ala Thr His
            420                 425                 430

Pro Glu Cys
        435

<210> SEQ ID NO 2
<211> LENGTH: 1308
<212> TYPE: DNA
<213> ORGANISM: Unknown
<220> FEATURE:
<223> OTHER INFORMATION: Kosmotoga olearia
<220> FEATURE:
<221> NAME/KEY: gene
<222> LOCATION: (1)..(1308)
<223> OTHER INFORMATION: Tagatose-bisphosphate aldolase

<400> SEQUENCE: 2
atgaaaaaac atcctcttca ggacattgtt tcattgcaaa acagggaat acccaaaggg     60 gttttctctg tatgtagtgc aatagattt gttattgaaa ccactctgga atatgcgaag    120
atgaaaggga caacggttct tatagaggcc acctgcaatc aggtaaacca gttcggtggc    180
tacaccggta tgactcctgc tgatttcaga gaaatggttt ttctatcgc tgaggatatt    240 ggacttccca aaaataaaat catccttggt ggcgaccatc ttggcccaaa tcctggaag    300 ggtcagccgt cagatcaggc tatgcgtaac gccattgaaa tgattcgaga atacgctaaa    360
gctgggttta ccaagcttca tctggatgcc agcatgcgtc ttgcagacga tccggggaac    420
gaaaacgagc cgctgaaccc ggaagttata gcggaaagaa cagctcttct ctgtcttgaa    480
gccgagaggg cttttaaaga atccgccggt tctctccggc tgtttacgt tattggtacg    540 gatgttccgc caccgggtgg agcgcaaaac gaaggtaaat cgattcatgt aaccagtgtt    600

-continued

```
caggattttg agcgtaccgt tgagttgacc aaaaaggcat ttttcgacca tggtttgtat    660
gaagcctggg gaagggtgat tgcggttgtt gtgcaaccgg gagtagaatt cgggaatgaa    720
catatattcg aatatgatag aaatcgagcg agagaactta ctgaggcgat aaaaaagcat    780
ccaaatatag tttttgaagg tcactcgaca gattatcaaa cggcaaaagc attgaaagaa    840
atggtagaag acgtgtagc catactcaag gttgggccag ctctaacatt tgcgctcaga    900
gaggcttttt ttgcgttgag cagcattgaa aaagagttat tttatgatac acccgggctt    960
tgttcaaact ttgttgaagt tgtcgagaga gcgatgcttg acaatccaaa acattgggaa   1020
aaatattacc agggagaaga gagagaaaat agattagccc gtaaatacag ctttctcgat   1080
cgcttgaggt attactggaa tcttcctgag gttagaacag cggtgaataa gctgataacc   1140
aaccttgaaa caaagaaat cccgttaacg cttataagcc agttcatgcc gatgcagtac   1200
caaaaaatca gaaacggttt gctaagaaag gatccaataa gccttataaa agatcgaatt   1260
acccttgttc ttgatgacta ctatttcgca actcaccctg aatgttga              1308
```

<210> SEQ ID NO 3
<211> LENGTH: 434
<212> TYPE: PRT
<213> ORGANISM: Unknown
<220> FEATURE:
<223> OTHER INFORMATION: Thermoanaerobacterium thermosaccharolyticum
<220> FEATURE:
<221> NAME/KEY: PEPTIDE
<222> LOCATION: (1)..(434)
<223> OTHER INFORMATION: Tagatose-bisphosphate aldolase

<400> SEQUENCE: 3

```
Met Ala Lys Glu His Pro Leu Lys Glu Leu Val Asn Lys Gln Lys Ser
1               5                   10                  15

Gly Ile Ser Glu Gly Ile Val Ser Ile Cys Ser Ser Asn Glu Phe Val
            20                  25                  30

Ile Glu Ala Ser Met Glu Arg Ala Leu Thr Asn Gly Asp Tyr Val Leu
        35                  40                  45

Ile Glu Ser Thr Ala Asn Gln Val Asn Gln Tyr Gly Gly Tyr Ile Gly
    50                  55                  60

Met Thr Pro Ile Glu Phe Lys Lys Phe Val Phe Ser Ile Ala Lys Lys
65                  70                  75                  80

Val Asp Phe Pro Leu Asp Lys Leu Ile Leu Gly Gly Asp His Leu Gly
                85                  90                  95

Pro Leu Ile Trp Lys Asn Glu Ser Ser Asn Leu Ala Leu Ala Lys Ala
            100                 105                 110

Ser Glu Leu Ile Lys Glu Tyr Val Leu Ala Gly Tyr Thr Lys Ile His
        115                 120                 125

Ile Asp Thr Ser Met Arg Leu Lys Asp Asp Thr Asp Phe Asn Thr Glu
    130                 135                 140

Ile Ile Ala Gln Arg Ser Ala Val Leu Leu Lys Ala Ala Glu Asn Ala
145                 150                 155                 160

Tyr Met Glu Leu Asn Lys Asn Lys Asn Val Leu His Pro Val Tyr
                165                 170                 175

Val Ile Gly Ser Glu Val Pro Ile Pro Gly Gly Ser Gln Gly Ser Asp
            180                 185                 190

Glu Ser Leu Gln Ile Thr Asp Ala Lys Asp Phe Glu Asn Thr Val Glu
        195                 200                 205

Ile Phe Lys Asp Val Phe Ser Lys Tyr Gly Leu Ile Asn Glu Trp Glu
```

-continued

```
               210                 215                 220
Asn Ile Val Ala Phe Val Val Gln Pro Gly Val Glu Phe Gly Asn Asp
225                 230                 235                 240

Phe Val His Glu Tyr Lys Arg Asp Glu Ala Lys Glu Leu Thr Asp Ala
                245                 250                 255

Leu Lys Asn Tyr Lys Thr Phe Val Phe Glu Gly His Ser Thr Asp Tyr
                260                 265                 270

Gln Thr Arg Glu Ser Leu Lys Gln Met Val Glu Asp Gly Ile Ala Ile
            275                 280                 285

Leu Lys Val Gly Pro Ala Leu Thr Phe Ala Leu Arg Glu Ala Leu Ile
        290                 295                 300

Ala Leu Asn Asn Ile Glu Asn Glu Leu Leu Asn Asn Val Asp Ser Ile
305                 310                 315                 320

Lys Leu Ser Asn Phe Thr Asn Val Leu Val Ser Glu Met Ile Asn Asn
                325                 330                 335

Pro Glu His Trp Lys Asn His Tyr Phe Gly Asp Asp Ala Arg Lys Lys
                340                 345                 350

Phe Leu Cys Lys Tyr Ser Tyr Ser Asp Arg Cys Arg Tyr Tyr Leu Pro
            355                 360                 365

Thr Arg Asn Val Lys Asn Ser Leu Asn Leu Leu Ile Arg Asn Leu Glu
        370                 375                 380

Asn Val Lys Ile Pro Met Thr Leu Ile Ser Gln Phe Met Pro Leu Gln
385                 390                 395                 400

Tyr Asp Asn Ile Arg Arg Gly Leu Ile Lys Asn Glu Pro Ile Ser Leu
                405                 410                 415

Ile Lys Asn Ala Ile Met Asn Arg Leu Asn Asp Tyr Tyr Tyr Ala Ile
                420                 425                 430

Lys Pro
```

<210> SEQ ID NO 4
<211> LENGTH: 1305
<212> TYPE: DNA
<213> ORGANISM: Unknown
<220> FEATURE:
<223> OTHER INFORMATION: Thermoanaerobacterium thermosaccharolyticum
<220> FEATURE:
<221> NAME/KEY: gene
<222> LOCATION: (1)..(1305)
<223> OTHER INFORMATION: Tagatose-bisphosphate aldolase

<400> SEQUENCE: 4

```
atggctaaag aacatccatt aaaggaatta gtaaataaac aaaaaagtgg tatatccgag     60
ggtatagttt ctatttgtag ttcaaatgaa tttgttattg aagcatctat ggagcgtgca    120
ttaacaaatg gtgattatgt tttaattgaa tcaacagcaa atcaggtgaa tcaatatggt    180
ggatatattg gtatgacacc tattgagttt aaaaaatttg tattttcaat agctaaaaaa    240
gtagattttc cattagataa attgattctt ggtggggatc atttaggccc attaatatgg    300
aaaaatgaat ctagtaattt ggcgttagca aaagcatccg agcttattaa agaatatgta    360
ttagccggat atactaaaat tcatatagac actagtatgc ggctaaaaga tgatactgat    420
tttaatacag aaattattgc tcaaagaagt gcagtattgt aaaggcagc ggaaatgca    480 tatatggaat gaataaaaa taataaaaat gttttacatc ctgtctatgt tataggaagt    540
gaagtcccaa tacctggggg cagccaaggc agtgatgaat cgctcccaat tactgatgct    600
aaggattttg aaaatacagt tgaaatattt aaagatgttt tttcaaaata tggattaatt    660
```

```
aatgagtggg aaaacatagt agcatttgtt gttcaaccag gagttgagtt tggaaatgat    720
tttgtacatg aatataaacg tgatgaagca aaagaattaa cagatgcact taaaaattat    780
aaaacatttg tttttgaagg acattctact gattatcaaa cacgtgaatc attaaaacaa    840
atggtggaag atggcattgc aatttaaaa gttggacctg cattaacatt tgcactacgt     900
gaagccttaa tagcactaaa taatatagaa aatgagttgc ttaataatgt agatagtata    960
aaattatcaa attttactaa tgtactcgta agtgaaatga tcaataaccc cgaacattgg   1020
aaaaatcatt attttggtga tgatgcaagg aaaaagtttc tatgtaaata tagttattcg   1080
gatagatgta ggtactattt accaactaga aatgtaaaaa actcattaaa tcttcttatt   1140
agaaatctag aaaatgtgaa aataccaatg acattaataa gtcaatttat gcctttgcaa   1200
tatgataata ttagaagagg actcataaaa aatgaaccaa tttctttaat taaaaatgca   1260
ataatgaacc gacttaatga ctattattat gctataaagc cgtaa                    1305
```

<210> SEQ ID NO 5
<211> LENGTH: 434
<212> TYPE: PRT
<213> ORGANISM: Unknown
<220> FEATURE:
<223> OTHER INFORMATION: Pseudoalteromonas sp. H103
<220> FEATURE:
<221> NAME/KEY: PEPTIDE
<222> LOCATION: (1)..(434)
<223> OTHER INFORMATION: Tagatose-bisphosphate aldolase

<400> SEQUENCE: 5

```
Met Arg Gly Asp Lys Arg Val Thr Thr Asp Phe Leu Lys Glu Ile Val
1               5                   10                  15

Gln Gln Asn Arg Ala Gly Gly Ser Arg Gly Ile Tyr Ser Val Cys Ser
            20                  25                  30

Ala His Arg Leu Val Ile Glu Ala Ser Met Gln Gln Ala Lys Ser Asp
        35                  40                  45

Gly Ser Pro Leu Leu Val Glu Ala Thr Cys Asn Gln Val Asn His Glu
    50                  55                  60

Gly Gly Tyr Thr Gly Met Thr Pro Ser Asp Phe Cys Lys Tyr Val Leu
65                  70                  75                  80

Asp Ile Ala Lys Glu Val Gly Phe Ser Gln Glu Gln Leu Ile Leu Gly
                85                  90                  95

Gly Asp His Leu Gly Pro Asn Pro Trp Thr Asp Leu Pro Ala Ala Gln
            100                 105                 110

Ala Met Glu Ala Ala Lys Lys Met Val Ala Asp Tyr Val Ser Ala Gly
        115                 120                 125

Phe Ser Lys Ile His Leu Asp Ala Ser Met Ala Cys Ala Asp Asp Val
    130                 135                 140

Glu Pro Leu Ala Asp Glu Val Ile Ala Gln Arg Ala Thr Ile Leu Cys
145                 150                 155                 160

Ala Ala Gly Glu Ala Ala Val Ser Asp Lys Asn Ala Ala Pro Met Tyr
                165                 170                 175

Ile Ile Gly Thr Glu Val Pro Val Pro Gly Gly Ala Gln Glu Asp Leu
            180                 185                 190

His Glu Leu Ala Thr Thr Asn Ile Asp Asp Leu Lys Gln Thr Ile Lys
        195                 200                 205

Thr His Lys Ala Lys Phe Ser Glu Asn Gly Leu Gln Asp Ala Trp Asp
    210                 215                 220

Arg Val Ile Gly Val Val Val Gln Pro Gly Val Glu Phe Asp His Ala
```

```
                225                 230                 235                 240
        Met Val Ile Gly Tyr Gln Ser Glu Lys Ala Gln Thr Leu Ser Lys Thr
                        245                 250                 255

Ile Leu Asp Phe Asp Asn Leu Val Tyr Glu Ala His Ser Thr Asp Tyr
                        260                 265                 270

Gln Thr Glu Thr Ala Leu Thr Asn Leu Val Asn Asp His Phe Ala Ile
                        275                 280                 285

Leu Lys Val Gly Pro Gly Leu Thr Tyr Ala Ala Arg Glu Ala Leu Phe
                        290                 295                 300

Ala Leu Ser Tyr Ile Glu Gln Glu Trp Ile Thr Asn Lys Pro Leu Ser
        305                 310                 315                 320

Asn Leu Arg Gln Val Leu Glu Glu Arg Met Leu Glu Asn Pro Lys Asn
                            325                 330                 335

Trp Ala Lys Tyr Tyr Thr Gly Thr Glu Gln Glu Gln Ala Phe Ala Arg
                        340                 345                 350

Lys Tyr Ser Phe Ser Asp Arg Ser Arg Tyr Tyr Trp Ala Asp Pro Ile
                        355                 360                 365

Val Asp Gln Ser Val Gln Thr Leu Ile Asn Asn Leu Thr Glu Gln Pro
                        370                 375                 380

Ala Pro Met Thr Leu Leu Ser Gln Phe Met Pro Leu Gln Tyr Ala Ala
        385                 390                 395                 400

Phe Arg Ala Gly Gln Leu Asn Asn Asp Pro Leu Ser Leu Ile Arg His
                        405                 410                 415

Trp Ile Gln Glu Val Val Ser Thr Tyr Ala Arg Ala Ser Gly Leu Ala
                        420                 425                 430

Val Lys

<210> SEQ ID NO 6
<211> LENGTH: 1305
<212> TYPE: DNA
<213> ORGANISM: Unknown
<220> FEATURE:
<223> OTHER INFORMATION: Pseudoalteromonas sp. H103
<220> FEATURE:
<221> NAME/KEY: gene
<222> LOCATION: (1)..(1305)
<223> OTHER INFORMATION: Tagatose-bisphosphate aldolase

<400> SEQUENCE: 6
atcagaggag ataaaagggt gactacagat tttctgaaag aaattgttca acaaaacaga      60
gccggtggta gcagaggtat ttactctgtt tgttctgcgc atcgccttgt tattgaagcg     120
tctatgcagc aagccaaaag cgatggctca ccactgttag tagaggcaac atgtaatcag     180
gttaatcacg aaggtggtta taccggtatg accccaagcg acttttgcaa atacgtgtta     240
gatattgcaa agaagtggg cttttcccaa gagcaactta ttttagggg cgaccactta      300 gggcctaacc cgtggactga cctaccagct gcacaggcaa tggaagcggc caaaaaaatg     360
gttgctgatt acgtaagtgc gggcttttca aaaatacatt tagatgcaag catggcatgt     420
gcagatgatg tagagccgct tgctgatgag gttatagcgc agcgcgccac tatttatgt     480 gctgccggcg aagctgctgt tagcgataaa aatgcagccc aatgtatat tattggtacc      540 gaagtgccgg taccaggtgg cgcacaagaa gatttacacg aacttgctac aaccaatatt     600
gatgatttaa acaaaccat taaaacccat aaagcaaaat ttagcgaaaa cggtttgcaa      660
gacgcatggg atagagtaat tggtgtagta gtgcagcctg gtgttgagtt tgaccacgcg     720
atggtaattg gctatcaaag cgaaaaagca caaacactaa gtaaaactat tttagatttt     780
```

-continued

```
gataatttgg tttatgaagc gcattcaacc gattatcaaa ccgaaacagc gttaactaac    840
ttggttaacg accactttgc tattttaaaa gtgggcccag ggcttactta tgcagcgcgc    900
gaagcgttgt ttgcacttag ttatattgag caagagtgga taaccaataa gcctctttct    960
aatttgcgcc aagtgcttga agagcgcatg ctcgaaaacc ctaaaaactg gctaagtat    1020 tacacaggta cagagcaaga gcaggccttt gcacgaaaat atagctttag cgatagatcg   1080
cgttactatt gggccgatcc tattgttgat caaagtgttc aaacactcat taataactta   1140
actgagcagc cagcgccaat gaccttgctg agtcaattta tgccacttca atatgcggca   1200
tttcgtgcag acaattaaa taacgatccg ctttctttga tcagacactg gatccaagaa   1260
gttgtatcaa cctacgcccg cgctagcgga cttgcagtaa aatag                   1305
```

<210> SEQ ID NO 7
<211> LENGTH: 426
<212> TYPE: PRT
<213> ORGANISM: Unknown
<220> FEATURE:
<223> OTHER INFORMATION: Thermanaerothrix daxensis
<220> FEATURE:
<221> NAME/KEY: PEPTIDE
<222> LOCATION: (1)..(426)
<223> OTHER INFORMATION: Tagatose-biphosphate aldolase

<400> SEQUENCE: 7

```
Met Val Thr Tyr Leu Asp Phe Val Val Leu Ser His Arg Phe Arg Arg
1               5                   10                  15

Pro Leu Gly Ile Thr Ser Val Cys Ser Ala His Pro Tyr Val Ile Glu
                20                  25                  30

Ala Ala Leu Arg Asn Gly Met Met Thr His Thr Pro Val Leu Ile Glu
            35                  40                  45

Ala Thr Cys Asn Gln Val Asn Gln Tyr Gly Gly Tyr Thr Gly Met Thr
        50                  55                  60

Pro Ala Asp Phe Val Arg Tyr Val Glu Asn Ile Ala Ala Arg Val Gly
65                  70                  75                  80

Ser Pro Arg Glu Asn Leu Leu Leu Gly Gly Asp His Leu Gly Pro Leu
                85                  90                  95

Val Trp Ala His Glu Pro Ala Glu Ser Ala Met Glu Lys Ala Arg Ala
                100                 105                 110

Leu Val Lys Ala Tyr Val Glu Ala Gly Phe Arg Lys Ile His Leu Asp
            115                 120                 125

Cys Ser Met Pro Cys Ala Asp Asp Arg Asp Phe Ser Pro Lys Val Ile
        130                 135                 140

Ala Glu Arg Ala Ala Glu Leu Ala Gln Val Ala Glu Ser Thr Cys Asp
145                 150                 155                 160

Val Met Gly Leu Pro Leu Pro Asn Tyr Val Ile Gly Thr Glu Val Pro
                165                 170                 175

Pro Ala Gly Gly Ala Lys Ala Glu Ala Glu Thr Leu Arg Val Thr Arg
            180                 185                 190

Pro Glu Asp Ala Ala Glu Thr Ile Ala Leu Thr Arg Ala Ala Phe Phe
        195                 200                 205

Lys Arg Gly Leu Glu Ser Ala Trp Glu Arg Val Ala Leu Val Val
    210                 215                 220

Gln Pro Gly Val Glu Phe Gly Asp His Gln Ile His Val Tyr Arg Arg
225                 230                 235                 240

Glu Glu Ala Gln Ala Leu Ser Arg Phe Ile Glu Ser Gln Pro Gly Leu
```

245                 250                 255
Val Tyr Glu Ala His Ser Thr Asp Tyr Gln Pro Arg Asp Ala Leu Arg
                260                 265                 270

Ala Leu Val Glu Asp His Phe Ala Ile Leu Lys Val Gly Pro Ala Leu
            275                 280                 285

Thr Phe Ala Phe Arg Glu Ala Val Phe Ala Leu Ala Ser Ile Glu Asp
        290                 295                 300

Trp Val Cys Asp Ser Pro Ser Arg Ile Leu Glu Val Leu Glu Thr Thr
305                 310                 315                 320

Met Leu Ala Asn Pro Val Tyr Trp Gln Lys Tyr Tyr Leu Gly Asp Glu
                325                 330                 335

Arg Ala Arg Arg Ile Ala Arg Gly Tyr Ser Phe Ser Asp Arg Ile Arg
            340                 345                 350

Tyr Tyr Trp Ser Ala Pro Ala Val Glu Gln Ala Phe Glu Arg Leu Arg
        355                 360                 365

Ala Asn Leu Asn Arg Val Ser Ile Pro Leu Val Leu Leu Ser Gln Tyr
    370                 375                 380

Leu Pro Asp Gln Tyr Arg Lys Val Arg Asp Gly Arg Leu Pro Asn Gln
385                 390                 395                 400

Phe Asp Ala Leu Ile Leu Asp Lys Ile Gln Ala Val Leu Glu Asp Tyr
                405                 410                 415

Asn Val Ala Cys Gly Val Arg Ile Gly Glu
            420                 425

<210> SEQ ID NO 8
<211> LENGTH: 1281
<212> TYPE: DNA
<213> ORGANISM: Unknown
<220> FEATURE:
<223> OTHER INFORMATION: Thermanaerothrix daxensis
<220> FEATURE:
<221> NAME/KEY: gene
<222> LOCATION: (1)..(1281)
<223> OTHER INFORMATION: Tagatose-biphosphate aldolase

<400> SEQUENCE: 8
atggttacct atttggattt tgtggtgctt tctcatcgtt ttaggcgccc cctgggcatt      60
acctcagtgt gttcggcgca tccgtatgtc attgaggcgg cgctgcgtaa tgggatgatg     120
acccatacac cggtcctaat cgaggccact tgcaatcaag tcaatcagta tgggggatat     180
acggggatga ccccggcaga tttcgtgcgg tatgtggaga atattgctgc acgggtaggc     240
tctccacgtg aaaacctcct tttgggtggc gatcatttgg acccctggt ctgggctcat     300 gaacctgctg agagtgccat ggaaaaagct cgagctctgg tcaaagccta tgtagaggct     360
ggttttcgca aaattcatct ggattgctca atgccctgtg cggatgatcg cgattttct      420 ccaaaggtca ttgctgagcg ggcagccgaa ttggctcagg tggcagagtc aacttgtgat     480
gttatgggct tgcccttgcc caactacgtc attgaaccg aggtgccccc agcaggtggc      540
gccaaggctg aagccgaaac tttgagggta acccgtccgg aggatgcagc ggagaccatt     600
gcactgacca gcggctttt ttcaagcga ggtttagagt ctgcctggga acgtgtagtg       660
gcgttagtag tgcaacccgg tgttgaattc ggagatcatc agattcatgt ttaccgccgt     720
gaggaagcgc aggctctttc ccgcttcatt gaaagccagc ccggcttagt ctatgaggct     780
cactccaccg actatcagcc ccgtgatgcg ctgcgggctt tggttgagga tcatttcgca    840
atcctgaagg tgggtccggc gctaaccttt gcttttcgtg aggcagtttt tgccctggcc     900

-continued

```
agtatcgagg attgggtatg cgattcaccc agtcgcatcc tggaagtttt ggaaacaacc    960
atgctggcca acccggtcta ctggcaaaag tattacttgg gcgatgagcg agcgcgtcgg   1020
attgccagag ggtatagttt cagcgatcgc attcgttatt attggagtgc accagcggtt   1080
gaacaggcct tgaacgcttt gcgggcaaat ctgaatcgtg tttcgatccc ccttgtcctt   1140
ctcagtcagt atttgccgga tcaatatcgc aaagtgcggg atggacggct gcctaaccag   1200
tttgatgctt tgattctgga taaaatccaa gccgtactgg aagactacaa tgtggcgtgt   1260
ggtgtgagga tagggagtg a                                              1281
```

<210> SEQ ID NO 9
<211> LENGTH: 431
<212> TYPE: PRT
<213> ORGANISM: Unknown
<220> FEATURE:
<223> OTHER INFORMATION: Acidobacteriales bacterium
<220> FEATURE:
<221> NAME/KEY: PEPTIDE
<222> LOCATION: (1)..(431)
<223> OTHER INFORMATION: Tagatose-biphosphate aldolase

<400> SEQUENCE: 9

```
Met Ser Asp Asn Leu Gln Val Phe Leu Arg Glu Ser Arg Gly Arg Arg
1               5                   10                  15

Gly Ile Tyr Ser Val Cys Ser Ala His Pro Arg Val Ile Glu Ala Ala
            20                  25                  30

Met Arg Gln Ala Gly Ala Asp Gly Thr His Leu Leu Glu Ala Thr
        35                  40                  45

Ser Asn Gln Val Asn Gln Ala Gly Gly Tyr Thr Gly Met Thr Pro Ala
    50                  55                  60

Met Phe Arg Asp Tyr Val Tyr Asp Ile Ala Gln Glu Ile Gly Phe Asp
65                  70                  75                  80

Arg Ser Arg Leu Ile Leu Gly Gly Asp His Leu Gly Pro Asn Pro Trp
                85                  90                  95

Gln Gln Leu Asp Ala Ser Thr Ala Met Gln Tyr Ala Glu Glu Met Val
            100                 105                 110

Arg Leu Tyr Ile Glu Ala Gly Phe Thr Lys Ile His Leu Asp Ala Ser
        115                 120                 125

Met Arg Cys Ala Asp Asp Ala Ala Ile Val Pro Asp Glu Val Met Ala
    130                 135                 140

Gly Arg Ala Ala Ala Leu Cys Ser Ala Ala Glu Ser Ala Arg Ala Arg
145                 150                 155                 160

Leu Gly Leu Ala Pro Val Val Tyr Val Ile Gly Thr Glu Val Pro Thr
                165                 170                 175

Pro Gly Gly Ala Ser His Ala Leu Asn Thr Leu Glu Val Thr Thr Arg
            180                 185                 190

Glu Ala Val Glu His Thr Leu Ser Val His Arg Lys Ala Phe His Asp
        195                 200                 205

Ala Gly Leu Asp Ala Ala Trp Gln Arg Val Ile Ala Val Val Val Gln
    210                 215                 220

Pro Gly Val Glu Phe Asp His Asp Ser Val Val Asp Tyr Asp Ala Ala
225                 230                 235                 240

Lys Ala Gly His Leu Gln Glu Phe Leu Gln Ala His Pro Glu Leu Val
                245                 250                 255

Met Glu Ala His Ser Ser Asp Tyr Gln Lys Pro Gln Ala Tyr Lys Glu
            260                 265                 270
```

| | | | | | | | | | | |
|---|---|---|---|---|---|---|---|---|---|---|
| Leu | Val | Arg | Asp | Gly | Phe | Ala | Ile | Leu | Lys | Val | Gly | Pro | Ala | Leu | Thr |
| | | | 275 | | | | 280 | | | | 285 | | | | |

Phe Ala Leu Arg Glu Met Leu Tyr Ala Leu Ala Ala Ile Glu Arg Glu
   290                       295                      300

Leu Val Pro Glu Ala Glu Gln Ser His Leu Val Glu Thr Met Glu Glu
305                     310                     315                   320

Ile Met Leu Ala His Pro Glu Asn Trp Gln Lys Tyr Tyr Arg Gly Ser
               325                     330                     335

Ala Glu Gln Gln Arg Leu Leu Arg Val Tyr Ser Tyr Ser Asp Arg Ile
           340                     345                    350

Arg Tyr Tyr Trp Gly Arg Pro Glu Ala Glu Ala Ala Val Thr Arg Leu
        355                     360                   365

Met Arg Asn Leu His Gln Thr Thr Ile Pro Glu Thr Leu Leu Ser Gln
   370                     375                     380

Tyr Cys Pro Arg Glu Tyr Glu Ala Met Arg Glu Gly Arg Leu Arg Asn
385                     390                     395                   400

Asp Pro Ala Glu Leu Thr Ile Ala Ser Ile Arg Thr Val Leu Glu Ser
           405                     410                    415

Tyr Ser Ser Ala Cys Arg Gly Asp Gly Ser Asn Ser Gly Lys Gln
        420                     425                   430

```
<210> SEQ ID NO 10
<211> LENGTH: 1296
<212> TYPE: DNA
<213> ORGANISM: Unknown
<220> FEATURE:
<223> OTHER INFORMATION: Acidobacteriales bacterium
<220> FEATURE:
<221> NAME/KEY: gene
<222> LOCATION: (1)..(1296)
<223> OTHER INFORMATION: Tagatose-biphosphate aldolase

<400> SEQUENCE: 10
```

| | | | | | |
|---|---|---|---|---|---|
| atgtccgaca | atttgcaggt | gtttcttcgt | gagtcccgag | gccggcgcgg | catctattcg | 60 |
| gtatgctccg | cgcatccccg | ggtgatcgag | gccgccatgc | ggcaagctgg | cgcagacggc | 120 |
| acgcatctgc | tgctggaagc | gacgtcgaat | caggtgaacc | aagccggagg | ctacaccggc | 180 |
| atgactcccg | cgatgtttcg | cgattacgtt | tatgacattg | cacaggagat | cggcttcgac | 240 |
| cgcagccgtt | tgattcttgg | cggagatcat | ttgggcccca | atccctgca | gcagctcgac | 300 |
| gccagcacag | cgatgcagta | tgcagaggag | atggttcgac | tgtacatcga | ggcaggattc | 360 |
| accaagattc | atctcgacgc | cagcatgcgt | tgtgccgacg | atgcggcaat | cgttcccgat | 420 |
| gaagtgatgg | caggacgcgc | cgccgcattg | tgcagcgcgg | ctgagtcggc | gcgagcacgg | 480 |
| ctgggactgg | cgccggtggt | ctacgtgatc | ggaaccgagg | ttccaacgcc | gggtggagca | 540 |
| agccatgctc | tcaacacgct | ggaggtaaca | acgcgggagg | cagtcgagca | tacgctgtcg | 600 |
| gttcatcgca | aagccttcca | cgatgcggga | ttggacgctg | catggcagcg | cgtgatcgcg | 660 |
| gtggtcgtgc | agccgggcgt | ggagttcgat | cacgatagcg | ttgtcgacta | tgacgccgca | 720 |
| aaagcgggcc | atttgcaaga | atttctacaa | gcccacccgg | aactggtgat | ggaggcacac | 780 |
| tccagcgatt | accagaagcc | gcaagcctac | aaggaactgg | tccgtgatgg | cttcgcgatc | 840 |
| ctgaaggtcg | ggcctgcgtt | gacgtttgcg | ctgcgggaga | tgctctacgc | gctggccgcc | 900 |
| atcgagcggg | aactggtgcc | ggaggcggag | cagtcccatc | tggtagagac | gatggaagag | 960 |
| atcatgctgc | tcatcccga | gaactggcag | aagtactatc | gcggaagcgc | agagcagcag | 1020 |
| cgattgctgc | gcgtctatag | ctacagcgac | cgcattcgct | attactgggg | acgtccggag | 1080 |

```
gccgaagctg ccgtcacgcg cctgatgcga aatctgcatc agacgacgat tcccgagact   1140
ctcctaagcc agtattgtcc gcgcgaatat gaggcaatgc gcgaaggaag actgcgaaac   1200
gatccggctg agttgacgat cgcgagcatt cgaactgtgc tggagtccta cagcagcgct   1260
tgtcgcggtg acggctcgaa ctccggtaaa cagtaa                             1296

<210> SEQ ID NO 11
<211> LENGTH: 420
<212> TYPE: PRT
<213> ORGANISM: Unknown
<220> FEATURE:
<223> OTHER INFORMATION: Rhodothermus profundi
<220> FEATURE:
<221> NAME/KEY: PEPTIDE
<222> LOCATION: (1)..(420)
<223> OTHER INFORMATION: Tagatose-biphosphate aldolase

<400> SEQUENCE: 11

Met Gln Ala His Val Leu Leu Ala Pro Ser Phe Glu Gln Leu Ala Asp
1               5                   10                  15

His Arg His Gly Phe Val Gly Trp Leu Val Asp Leu Leu Arg Gly Pro
            20                  25                  30

Leu Ala Tyr Arg His Thr Leu Leu Ala Val Cys Pro Asn Ser Glu Ala
        35                  40                  45

Val Thr Arg Ala Ala Leu Glu Ala Ala Arg Glu Ala Asn Ala Pro Leu
    50                  55                  60

Phe Phe Ala Ala Thr Leu Asn Gln Val Asp Leu Asp Gly Gly Tyr Thr
65                  70                  75                  80

Gly Trp Thr Pro Ala Thr Leu Ala Arg Phe Val Ala Asp Glu Arg Ile
                85                  90                  95

Arg Leu Gly Leu Arg Ala Pro Val Val Leu Gly Leu Asp His Gly Gly
            100                 105                 110

Pro Trp Lys Lys Asp Trp His Val Arg Asn Arg Leu Pro Tyr Glu Ala
        115                 120                 125

Thr Leu Gln Ala Val Leu Arg Ala Ile Glu Ala Cys Leu Asp Ala Gly
    130                 135                 140

Tyr Gly Leu Leu His Leu Asp Pro Thr Val Asp Leu Glu Leu Pro Pro
145                 150                 155                 160

Gly Thr Pro Val Pro Ile Pro Arg Ile Val Glu Arg Thr Val Ala Leu
                165                 170                 175

Leu Gln His Ala Glu Thr Tyr Arg Gln Gln Arg Arg Leu Pro Pro Val
            180                 185                 190

Ala Tyr Glu Val Gly Thr Glu Glu Val Gly Gly Leu Gln Ala Glu
        195                 200                 205

Ala Arg Met Ala Glu Phe Leu Asp Arg Leu Trp Thr Val Leu Asp Arg
    210                 215                 220

Glu Gly Leu Pro Arg Pro Val Phe Val Val Gly Asp Ile Gly Thr Arg
225                 230                 235                 240

Leu Asp Thr His Thr Phe Asp Phe Glu Arg Ala Arg Leu Asp Ala
                245                 250                 255

Leu Val Arg Arg Tyr Gly Ala Leu Ile Lys Gly His Tyr Thr Asp Gly
            260                 265                 270

Val Asp Arg Leu Asp Leu Tyr Pro Gln Ala Gly Ile Gly Gly Ala Asn
        275                 280                 285

Val Gly Pro Gly Leu Ala Ala Ile Glu Phe Glu Ala Leu Glu Ala Leu
    290                 295                 300
```

```
Val Ala Glu Ala His Arg Arg Lys Leu Pro Val Thr Phe Asp Arg Thr
305                 310                 315                 320

Ile Arg Gln Ala Val Ile Glu Ser Gly Arg Trp Gln Lys Trp Leu Arg
            325                 330                 335

Pro Glu Glu Lys Gly Arg Pro Phe Glu Ala Leu Pro Pro Glu Arg Gln
        340                 345                 350

Arg Trp Leu Val Ala Thr Gly Ser Arg Tyr Val Trp Thr His Pro Ala
    355                 360                 365

Val Arg Gln Ala Arg His Gln Leu Tyr Gln Val Leu Ala Pro Trp Leu
370                 375                 380

Asp Ala Asp Ala Phe Val Arg Ala Arg Ile Lys Ala Arg Leu Met Asp
385                 390                 395                 400

Tyr Phe Arg Ala Phe Asn Leu Ile Gly Phe Asn Glu Arg Leu Gln Ala
                405                 410                 415

Phe Leu Pro Asn
            420

<210> SEQ ID NO 12
<211> LENGTH: 1263
<212> TYPE: DNA
<213> ORGANISM: Unknown
<220> FEATURE:
<223> OTHER INFORMATION: Rhodothermus profundi
<220> FEATURE:
<221> NAME/KEY: gene
<222> LOCATION: (1)..(1263)
<223> OTHER INFORMATION: Tagatose-biphosphate aldolase

<400> SEQUENCE: 12
atgcaggcgc acgtcctgct tgccccttcg ttcgagcagc tagcagacca caggcacgga      60
tttgttggct ggttggtcga tttgctgcgc ggaccgctgg cttaccggca cacgctgctg     120
gccgtatgtc ccaattccga agccgtaacg cgcgccgccc tggaagctgc gcgcgaagcc     180
aacgccccgc tatttttgc ggctaccctg aaccaggtcg acctggatgg cggatatacc     240
ggctggaccc cggccacgct ggctcgtttt gttgccgacg agcgcatccg cctgggcctt     300
cgcgcccctg tcgtacttgg tctggatcac ggtggcccct ggaaaaagga ttggcatgtc     360
cgcaaccgtc ttccgtacga ggcaacgctc caggcggtgc ttcgcgcgat tgaggcctgc     420
ctcgacgcag ttatgggct gcttcatctg gacccgacgg tagatctgga attgccgccc     480
ggcacacccg tccccatccc acgtattgtc gaacgaacgg tagcgctttt acaacatgct     540
gaaacgtatc gccaacagcg tcgcctgccc ccggtcgcct acgaggtagg cacggaggag     600
gttggcggcg gcctgcaggc tgaggcgcga atggcagaat ttctggatcg actctggacc     660
gtcctggatc gggaagggct accccgtccg gtgtttgtgg tgggtgacat ggcacccgg     720 cttgacacgc acaccttcga ctttgaacgc gcccgtcgcc tggatgccct ggtgcgccgc     780
tacggtgccc tgatcaaggg gcactacacc gatgagtag accgcctgga tctatatcca     840
caggcgggta tcggtggagc aaacgtgggg cctggcctgg ctgctatcga gtttgaagcg     900
ctggaggccc tggtggccga agcgcaccgc cgcaagctgc ccgttacctt tgaccggacc     960
atccgccagg ctgtcattga agtggacgc tggcaaaaat ggctgcgccc tgaagagaaa    1020
ggacgtccct ttgaagcatt acctccagaa cgccagcggt ggctggtcgc tacaggcagc    1080
cgctacgtgt ggacgcaccc ggctgtccgg caggcgcgcc atcaattgta tcaggtgctc    1140
gctccctggc tcgatgccga tgcttttgtg cgcgcgcgca tcaaggcccg cctgatggac    1200
```

```
tacttccgcg ctttcaacct gataggcttc aatgaacggc tgcaggcctt tttacctaat    1260
tga                                                                  1263
```

<210> SEQ ID NO 13
<211> LENGTH: 420
<212> TYPE: PRT
<213> ORGANISM: Unknown
<220> FEATURE:
<223> OTHER INFORMATION: Rhodothermus marinus
<220> FEATURE:
<221> NAME/KEY: PEPTIDE
<222> LOCATION: (1)..(420)
<223> OTHER INFORMATION: Tagatose-biphosphate aldolase

<400> SEQUENCE: 13

```
Met Gln Ala Gln Ala Leu Leu Thr Val Pro Phe Asp Arg Val Ala Thr
1               5                   10                  15

His Ala Arg Gly Phe Val Gly Trp Val Ala Glu Leu Leu Gln Gly Pro
            20                  25                  30

Leu Ala Tyr Gln His Thr Leu Leu Ala Val Cys Pro Asn Ser Glu Ala
        35                  40                  45

Val Thr Arg Ala Ala Leu Glu Ala Ala Glu Ala Asn Ala Pro Leu
    50                  55                  60

Leu Phe Ala Ala Thr Leu Asn Gln Val Asp Leu Asp Gly Gly Tyr Thr
65                  70                  75                  80

Gly Trp Thr Pro Ala Thr Leu Ala Arg Phe Val Ala Asp Glu Leu Ala
                85                  90                  95

Arg Leu Asp Leu His Ile Pro Val Val Leu Gly Leu Asp His Gly Gly
            100                 105                 110

Pro Trp Lys Lys Asp Leu His Ala Arg Asn Arg Leu Ser Phe Glu Glu
        115                 120                 125

Thr Phe Gln Ala Val Leu Arg Ala Ile Glu Ala Cys Leu Asp Ala Gly
130                 135                 140

Tyr Gly Leu Leu His Leu Asp Pro Thr Val Asp Leu Glu Leu Ser Pro
145                 150                 155                 160

Gly Thr Pro Val Pro Ile Pro Arg Ile Val Glu Arg Ser Val Ala Leu
                165                 170                 175

Leu Arg His Ala Glu Thr Tyr Arg Leu Arg Arg Asn Leu Pro Pro Val
            180                 185                 190

Ala Tyr Glu Val Gly Thr Glu Glu Val Gly Gly Leu Gln Ala Glu
        195                 200                 205

Ala Arg Met Ala Glu Phe Leu Asp Arg Leu Trp Thr Ala Leu Asp Arg
    210                 215                 220

Glu Gly Leu Pro His Pro Val Phe Val Val Gly Asp Ile Gly Thr Arg
225                 230                 235                 240

Leu Asp Thr Arg Thr Phe Asp Phe Glu Arg Ala Arg Arg Leu Asp Ala
                245                 250                 255

Leu Val Arg Arg Tyr Gly Ala Leu Ile Lys Gly His Tyr Thr Asp Asp
            260                 265                 270

Val Asp Arg Leu Asp Leu Tyr Pro Lys Ala Gly Ile Gly Gly Ala Asn
        275                 280                 285

Val Gly Pro Gly Leu Ala Ala Ile Glu Phe Glu Ala Leu Glu Ala Leu
    290                 295                 300

Val Glu Glu Ala Arg Arg Gly Leu Ser Val Thr Phe Asp Gln Ala
305                 310                 315                 320

Ile Arg Arg Ala Val Val Glu Ser Gly Arg Trp Thr Lys Trp Leu Gln
```

|  |  |  | 325 |  |  |  |  | 330 |  |  |  |  | 335 |  |
|---|---|---|---|---|---|---|---|---|---|---|---|---|---|---|
| Pro | Glu | Glu | Lys | Gly | Gln | Pro | Phe | Asp | Ala | Leu | Asp | Pro | Glu | Arg | Gln |
|  |  |  | 340 |  |  |  |  | 345 |  |  |  |  | 350 |  |  |
| Arg | Trp | Leu | Val | Ala | Thr | Gly | Ser | Arg | Tyr | Val | Trp | Thr | His | Pro | Ala |
|  |  |  | 355 |  |  |  |  | 360 |  |  |  |  | 365 |  |  |
| Val | Leu | Gln | Ala | Arg | Arg | Glu | Leu | Tyr | Glu | Ala | Leu | Ala | Pro | Trp | Leu |
|  |  |  | 370 |  |  |  |  | 375 |  |  |  |  | 380 |  |  |
| Asp | Ala | Asp | Ala | Phe | Val | Arg | Thr | Arg | Ile | Lys | Ala | Arg | Leu | Met | Asp |
| 385 |  |  |  |  | 390 |  |  |  |  | 395 |  |  |  |  | 400 |
| Tyr | Phe | Arg | Ala | Phe | Asn | Leu | Ile | His | Phe | Asn | Glu | Arg | Leu | Gln | Ala |
|  |  |  |  | 405 |  |  |  |  | 410 |  |  |  |  | 415 |  |
| Phe | Leu | Pro | Glu |  |  |  |  |  |  |  |  |  |  |  |  |
|  |  |  | 420 |  |  |  |  |  |  |  |  |  |  |  |  |

```
<210> SEQ ID NO 14
<211> LENGTH: 1263
<212> TYPE: DNA
<213> ORGANISM: Unknown
<220> FEATURE:
<223> OTHER INFORMATION: Rhodothermus marinus
<220> FEATURE:
<221> NAME/KEY: gene
<222> LOCATION: (1)..(1263)
<223> OTHER INFORMATION: Tagatose-biphosphate aldolase

<400> SEQUENCE: 14
```

| | |
|---|---|
| atgcaggcgc aggccctgct gaccgttcca tttgatcggg tggcgaccca cgcacgcggg | 60 |
| tttgtgggct gggtggccga actgctgcag gggcccctgg cctatcagca tacgctgctg | 120 |
| gctgtctgtc ccaattcgga agcggtaaca cgggccgcgc tggaggccgc cgccgaggcc | 180 |
| aacgccccgc tgcttttttgc cgccacgctg aaccaggtgg acctcgacgg cggctacacc | 240 |
| ggctggacgc ccgccacgct ggcccggttc gtggcggacg aactggcccg cctggacctg | 300 |
| cacatccccg tcgtgctcgg cctggaccac ggcggcccct ggaaaaagga tctgcacgcc | 360 |
| cgcaaccgat tgtcctttga ggaaaccttc caggccgtgc tgcgggccat cgaggcctgt | 420 |
| ctggatgccg gctacggcct gctgcacctg atccgacgg tcgatctgga gctatcgccc | 480 |
| ggcacgccgg tgcccatccc gcgcattgtc gaacgctcgg tagcgctttt cgtcatgcc | 540 |
| gaaacctatc gacttcgacg taacctgccg ccggtcgcct acgaggtggg caccgaagaa | 600 |
| gtcggcggcg gcctgcaggc cgaagcgcgc atggcggagt ttctggatcg cctctggacc | 660 |
| gcactggacc gggaaggcct gccccatcca gtcttcgtgg tgggcgacat cggcaccccgg | 720 |
| ctcgacacgc gcacgttcga cttcgagcgg gcccgacggc tggacgcgct ggtgcgccgc | 780 |
| tacggtgccc tcatcaaagg gcactacacc gacgacgtgg atcgcctcga tctgtacccg | 840 |
| aaggcgggca tcggcggggc caacgtgggc ccgggcctgg ccgccatcga gtttgaagcg | 900 |
| ctggaggcgc tggtggagga gcccgtcgc gcggtctttt cggtgacgtt cgatcaggcc | 960 |
| atccgccggg ccgtcgtcga aagcggacgc tggacgaagt ggctccaacc ggaagagaaa | 1020 |
| ggccagccgt tcgatgcgct ggatcccgag cggcaacgct ggctggtggc caccggcagc | 1080 |
| cgctacgtgt ggacgcatcc ggccgtcctg caggcccgcc gcgaactcta cgaggcgctc | 1140 |
| gcccctggc tcgatgccga cgctttcgtg cgcacgcgca tcaaagcacg cctgatggac | 1200 |
| tactttcgtg ccttcaacct gatccatttc aacgagcggc tgcaggcctt ctcccccgaa | 1260 |
| tga | 1263 |

<210> SEQ ID NO 15
<211> LENGTH: 448
<212> TYPE: PRT
<213> ORGANISM: Unknown
<220> FEATURE:
<223> OTHER INFORMATION: Limnochorda pilosa
<220> FEATURE:
<221> NAME/KEY: PEPTIDE
<222> LOCATION: (1)..(448)
<223> OTHER INFORMATION: Tagatose-biphosphate aldolase

<400> SEQUENCE: 15

```
Met Gln Thr Ser Thr Ala Tyr Val Arg Gln Val Ile Trp Gly Gln Gly
1               5                   10                  15

Thr Arg Asp Pro Arg Gly Ile Tyr Ser Val Cys Thr Ala Asp Pro Leu
            20                  25                  30

Val Leu Arg Ala Ala Leu Lys Gln Ala Val Glu Asp Gly Ser Pro Ala
        35                  40                  45

Leu Ile Glu Ala Thr Ser Asn Gln Val Asn Gln Phe Gly Gly Tyr Thr
    50                  55                  60

Gly Met Glu Pro Pro Ala Phe Val Glu Phe Val Leu Gly Leu Ala Arg
65                  70                  75                  80

Glu Met Gly Leu Pro Pro Glu Arg Leu Ile Leu Gly Gly Asp His Leu
                85                  90                  95

Gly Pro Asn Pro Trp Gln Arg Leu Ala Ala Glu Glu Ala Met Arg His
            100                 105                 110

Ala Cys Asp Leu Val Glu Ala Phe Val Ala Cys Gly Phe Thr Lys Ile
        115                 120                 125

His Leu Asp Ala Ser Met Pro Leu Gly Glu Glu Arg Ala Gly Gly Ala
    130                 135                 140

Leu Ser Lys Arg Val Val Ala Glu Arg Thr Ala Gln Leu Cys Glu Ala
145                 150                 155                 160

Ala Glu Ala Ala Phe Arg Lys Arg Ser Gln Ala Glu Gly Ala Ser Ala
                165                 170                 175

Pro Pro Leu Tyr Val Ile Gly Ser Asp Val Pro Pro Gly Gly Glu
            180                 185                 190

Thr Ser Gly Ser Gln Gly Pro Lys Val Thr Thr Pro Glu Glu Phe Glu
        195                 200                 205

Glu Thr Val Ala Leu Thr Arg Ala Thr Phe His Asp Arg Gly Leu Asp
    210                 215                 220

Asp Ala Trp Gly Arg Val Ile Ala Val Val Gln Pro Gly Val Asp
225                 230                 235                 240

Phe Gly Glu Trp Gln Val His Pro Tyr Asp Arg Ala Ala Ala Ser
                245                 250                 255

Leu Thr Arg Ala Leu Thr Gln His Pro Gly Leu Ala Phe Glu Gly His
            260                 265                 270

Ser Thr Asp Tyr Gln Thr Pro Gly Arg Leu Arg Gln Met Ala Glu Asp
        275                 280                 285

Gly Ile Ala Ile Leu Lys Val Gly Pro Ala Leu Thr Phe Ala Lys Arg
    290                 295                 300

Glu Ala Leu Phe Ala Leu Asn Ala Leu Glu Ser Glu Val Leu Gly Thr
305                 310                 315                 320

Asp Gly Arg Ala Arg Arg Ser Asn Val Glu Ala Ala Leu Glu Glu Ala
                325                 330                 335

Met Leu Ala Asp Pro Arg His Trp Ser Ala Tyr Tyr Ser Gly Asp Glu
            340                 345                 350
```

```
His Glu Leu Arg Leu Lys Arg Lys Tyr Gly Leu Ser Asp Arg Cys Arg
            355                 360                 365

Tyr Tyr Trp Pro Val Pro Ser Val Gln Glu Ala Val Gln Arg Leu Leu
    370                 375                 380

Gly Asn Leu Arg Glu Ala Gly Ile Pro Leu Pro Leu Leu Ser Gln Phe
385                 390                 395                 400

Leu Pro Arg Gln Tyr Glu Arg Val Arg Glu Gly Val Leu Arg Asn Asp
                405                 410                 415

Pro Glu Glu Leu Val Leu Asp Arg Ile Arg Asp Val Leu Arg Gly Tyr
                420                 425                 430

Ala Ala Ala Val Gly Thr Gly Ala Arg Arg Ala Glu Pro Ser Pro Ala
            435                 440                 445

<210> SEQ ID NO 16
<211> LENGTH: 1347
<212> TYPE: DNA
<213> ORGANISM: Unknown
<220> FEATURE:
<223> OTHER INFORMATION: Limnochorda pilosa
<220> FEATURE:
<221> NAME/KEY: gene
<222> LOCATION: (1)..(1347)
<223> OTHER INFORMATION: Tagatose-biphosphate aldolase

<400> SEQUENCE: 16
atgcaaacct cgacggcgta cgtgaggcag gtcatttggg gtcaagggac gagggacccc        60
cgcggcatct actcggtctg taccgcagac ccctcgtcc ttcgggccgc cctcaagcag       120
gcggtggagg atggctcccc cgcgctgatc gaggcgacgt ccaaccaggt gaaccagttc       180
ggcgggtata cggggatgga ccccggcg ttcgtggagt tcgtgctggg acttgcccgc        240
gagatgggac tcccgcccga gcggctgatc ctcggggcg atcacctcgg ccccaaccca        300
tggcagcggc tggcggccga agaggccatg cggcatgcct gcgacctcgt cgaggccttc       360
gtggcctgcg gcttcaccaa gattcacctg gacgccagca tgcccctggg ggaggaacgg       420
gcaggcggtg cgctttcgaa acgggtggtg gccgaacgga ccgcccagct ctgcgaggcg       480
gccgaggcgg ccttcaggaa gcggtcccag gcggaggggg cgtcggcgcc tccgctctac       540
gtcatcggct ccgacgtgcc tccgcccggc ggcgagacct ccgggagcca ggggcccaag       600
gtgaccacgc cggaggagtt cgaggagacg gtcgcgctga gcggggcgac ctttcacgat       660
cggggcctgg acgacgcctg ggacggggtg atcgccgtgg tggtccagcc ggggggtggac       720 ttcggcgagt ggcaggttca cccctacgat cggccgccg cggcgagcct tacccgagcc       780
ttgacgcagc atccggggct ggccttcgaa gggcactcca ccgactacca gacgccgggg       840
cggcttcgcc agatggcgga agacggcatc gccatcctga aggtggggcc ggccctcacc       900
ttcgccaagc gggaagcgct cttcgccctg aacgccctgg agtccgaagt gctggggacg       960
gacggccgag cacggcgctc caacgtcgaa gccgccctcg aagaggcgat gctcgccgat      1020
ccccgtcact ggagcgccta ctacagcggg gacgagcacg agctccgtct caagcggaag      1080
tacggcctct ccgaccggtg tcgctactac tggcccgtcc cttcggtgca ggaggccgtc      1140
cagcgcctcc ttggcaacct gcgcgaggcg gggatcccct tgcccctgct gagccagttc      1200
ctgccgcgcc agtacgagcg ggtgcgggag ggcgtcctgc gcaacgaccc ggaggagctg      1260
gtcctggacc ggattcgtga cgtgttgcgg ggatatgcgg cggccgtggg gacgggcgct      1320
aggcgggcgg agccatcacc cgcgtga                                          1347
```

<210> SEQ ID NO 17
<211> LENGTH: 453
<212> TYPE: PRT
<213> ORGANISM: Unknown
<220> FEATURE:
<223> OTHER INFORMATION: Caldithrix abyssi
<220> FEATURE:
<221> NAME/KEY: PEPTIDE
<222> LOCATION: (1)..(453)
<223> OTHER INFORMATION: Tagatose-biphosphate aldolase

<400> SEQUENCE: 17

```
Met Ser Leu His Pro Leu Asn Lys Leu Ile Glu Arg His Lys Lys Gly
1               5                   10                  15

Thr Pro Val Gly Ile Tyr Ser Val Cys Ser Ala Asn Pro Phe Val Leu
            20                  25                  30

Lys Ala Ala Met Leu Gln Ala Gln Lys Asp Gln Ser Leu Leu Leu Ile
        35                  40                  45

Glu Ala Thr Ser Asn Gln Val Asp Gln Phe Gly Gly Tyr Thr Gly Met
    50                  55                  60

Arg Pro Glu Asp Phe Lys Thr Met Thr Leu Glu Leu Ala Ala Glu Asn
65                  70                  75                  80

Asn Tyr Asp Pro Gln Gly Leu Ile Leu Gly Gly Asp His Leu Gly Pro
                85                  90                  95

Asn Arg Trp Thr Lys Leu Ser Ala Ser Arg Ala Met Asp Tyr Ala Arg
            100                 105                 110

Glu Gln Ile Ala Ala Tyr Val Lys Ala Gly Phe Ser Lys Ile His Leu
        115                 120                 125

Asp Ala Thr Met Pro Leu Gln Asn Asp Ala Thr Asp Ser Ala Gly Arg
    130                 135                 140

Leu Pro Val Glu Thr Ile Ala Gln Arg Thr Ala Glu Leu Cys Ala Val
145                 150                 155                 160

Ala Glu Gln Thr Tyr Arg Gln Ser Asp Gln Leu Phe Pro Pro Pro Val
                165                 170                 175

Tyr Ile Val Gly Ser Asp Val Pro Ile Pro Gly Gly Ala Gln Glu Ala
            180                 185                 190

Leu Asn Gln Ile His Ile Thr Glu Val Lys Glu Val Gln Thr Ile
        195                 200                 205

Asp His Val Arg Arg Ala Phe Glu Lys Asn Gly Leu Glu Ala Ala Tyr
    210                 215                 220

Glu Arg Val Cys Ala Val Val Gln Pro Gly Val Glu Phe Ala Asp
225                 230                 235                 240

Gln Ile Val Phe Glu Tyr Ala Pro Asp Arg Ala Ala Leu Lys Asp
                245                 250                 255

Phe Ile Glu Ser His Ser Gln Leu Val Tyr Glu Ala His Ser Thr Asp
            260                 265                 270

Tyr Gln Thr Ala Pro Leu Leu Arg Gln Met Val Lys Asp His Phe Ala
        275                 280                 285

Ile Leu Lys Val Gly Pro Ala Leu Thr Phe Ala Leu Arg Glu Ala Ile
    290                 295                 300

Phe Ala Leu Ala Phe Met Glu Lys Glu Leu Leu Pro Leu His Arg Ala
305                 310                 315                 320

Leu Lys Pro Ser Ala Ile Leu Glu Thr Leu Asp Gln Thr Met Asp Lys
                325                 330                 335

Asn Pro Ala Tyr Trp Gln Lys His Tyr Gly Gly Thr Lys Glu Glu Val
            340                 345                 350
```

Arg Phe Ala Gln Arg Phe Ser Leu Ser Asp Arg Ile Arg Tyr Tyr Trp
            355                 360                 365

Pro Phe Pro Lys Val Gln Lys Ala Leu Arg Gln Leu Leu Lys Asn Leu
    370                 375                 380

Gln Gln Ile Ser Ile Pro Leu Thr Leu Val Ser Gln Phe Met Pro Glu
385                 390                 395                 400

Glu Tyr Gln Arg Ile Arg Gln Gly Thr Leu Thr Asn Asp Pro Gln Ala
                405                 410                 415

Leu Ile Leu Asn Lys Ile Gln Ser Val Leu Lys Gln Tyr Ala Glu Ala
            420                 425                 430

Thr Gln Ile Gln Asn Ser Leu Thr Phe Thr Gln Asn Gln Asn Ser Leu
        435                 440                 445

Ala Met Glu Arg Leu
    450

<210> SEQ ID NO 18
<211> LENGTH: 1362
<212> TYPE: DNA
<213> ORGANISM: Unknown
<220> FEATURE:
<223> OTHER INFORMATION: Caldithrix abyssi
<220> FEATURE:
<221> NAME/KEY: gene
<222> LOCATION: (1)..(1362)
<223> OTHER INFORMATION: Tagatose-biphosphate aldolase

<400> SEQUENCE: 18

```
atgagtctgc atcctttaaa taaattaatc gagcgacaca aaaaaggaac gccggtcggt      60
atttattccg tctgttcggc caatcccttt gttttgaaag cggccatgct acaggcgcaa     120
aaggatcagt ctttgctact tattgaggcc acttccaacc aggtagatca attcggcggt     180
tacaccggca tgcggcccga agattttaaa acaatgacgc ttgaactggc agccgaaaac     240
aattacgatc acagggatt aatcctgggc ggcgaccatc tggggcccaa ccgctggaca     300
aaactgagcg cctcccgggc catggactac gccagagagc agattgccgc ttatgttaaa     360
gccggctttt ccaaaatcca cttagacgcc accatgccct tgcaaaacga tgccacagat     420
tccgccggcc gccttccagt cgaaacaatc gctcaacgta ccgcagaatt atgcgccgtg     480
gccgaacaaa cttaccggca gagcgaccaa ctctttccgc cgcctgttta cattgtcggc     540
agcgacgtgc ccatcccggg cggcgcgcaa gaagcgctga accagatcca tattacggag     600
gtaaaagagg ttcaacagac cattgatcac gtgcggcggg cctttgaaaa aaacggcctg     660
gaagcggctt acgaaagagt ttgcgccgtt gtcgtgcagc caggcgttga attcgccgat     720
caaatcgttt ttgaatacgc tcccgacaga gcggcggcct aaaagatttt tattgaaagc     780
cattcgcagc tggtttatga agcgcactct actgattacc agaccgcacc tcttttgcgc     840
cagatggtaa agatcacttt gccattttta aaggtcgggc ctgcgctcac ctttgccctg     900
cgcgaagcca ttttttgctct ggcctttatg gaaaaaaagagc ttttgccatt gcacagagcg     960
ctcaaacctt ctgccattct ggaaacgctg gaccaaacga tggacaaaaa ccctgcttac    1020
tggcaaaagc attacggcgg aacaaaggaa gaagtacgct ttgcgcagcg gtttagcctg    1080
agcgaccgca ttcgttacta ctggccgttt ccaaggttc aaaaggccct gcgccaattg    1140
ctaaaaaact tgcaacaaat ttccattcct ctaactttgg taagccagtt catgccagag    1200
gaataccaac gtattcgcca aggaacgtta accaacgatc cgcaggcgct gattttgaac    1260
aaaattcaaa gcgtattaaa gcaatacgcg gaggcgacgc aaattcaaaa ctcttttgaca    1320
```
ttcacgcaaa atcaaaattc attagcaatg gagcgactat ga          1362

<210> SEQ ID NO 19
<211> LENGTH: 429
<212> TYPE: PRT
<213> ORGANISM: Unknown
<220> FEATURE:
<223> OTHER INFORMATION: Caldicellulosiruptor kronotskyensis
<220> FEATURE:
<221> NAME/KEY: PEPTIDE
<222> LOCATION: (1)..(429)
<223> OTHER INFORMATION: Tagatose-biphosphate aldolase

<400> SEQUENCE: 19

Met Ser Pro Gln Asn Pro Leu Ile Gly Leu Phe Lys Asn Arg Glu Lys
1               5                   10                  15

Glu Phe Lys Gly Ile Ile Ser Val Cys Ser Ser Asn Glu Ile Val Leu
            20                  25                  30

Glu Ala Val Leu Lys Arg Met Lys Asp Thr Asn Leu Pro Ile Ile Ile
        35                  40                  45

Glu Ala Thr Ala Asn Gln Val Asn Gln Phe Gly Gly Tyr Ser Gly Leu
    50                  55                  60

Thr Pro Ser Gln Phe Lys Glu Arg Val Ile Lys Ile Ala Gln Lys Val
65                  70                  75                  80

Asp Phe Pro Leu Glu Arg Ile Ile Leu Gly Gly Asp His Leu Gly Pro
                85                  90                  95

Phe Val Trp Arg Asp Gln Glu Pro Glu Ile Ala Met Glu Tyr Ala Lys
            100                 105                 110

Gln Met Ile Lys Glu Tyr Ile Lys Ala Gly Phe Thr Lys Ile His Ile
        115                 120                 125

Asp Thr Ser Met Pro Leu Lys Gly Glu Asn Ser Ile Asp Asp Glu Ile
130                 135                 140

Ile Ala Lys Arg Thr Ala Val Leu Cys Arg Ile Ala Glu Glu Cys Phe
145                 150                 155                 160

Glu Lys Ile Ser Ile Asn Asn Pro Tyr Ile Thr Arg Pro Val Tyr Val
                165                 170                 175

Ile Gly Ala Asp Val Pro Pro Gly Gly Glu Ser Ser Ile Cys Gln
            180                 185                 190

Thr Ile Thr Thr Lys Asp Glu Leu Glu Arg Ser Leu Glu Tyr Phe Lys
        195                 200                 205

Glu Ala Phe Lys Lys Glu Gly Ile Glu His Val Phe Asp Tyr Val Val
    210                 215                 220

Ala Val Val Ala Asn Phe Gly Val Glu Phe Gly Ser Asp Glu Ile Val
225                 230                 235                 240

Asp Phe Asp Met Glu Lys Val Lys Pro Leu Lys Glu Leu Leu Ala Lys
                245                 250                 255

Tyr Asn Ile Val Phe Glu Gly His Ser Thr Asp Tyr Gln Thr Lys Glu
            260                 265                 270

Asn Leu Lys Arg Met Val Glu Cys Gly Ile Ala Ile Leu Lys Val Gly
        275                 280                 285

Pro Ala Leu Thr Phe Thr Leu Arg Glu Ala Leu Val Ala Leu Ser His
    290                 295                 300

Ile Glu Glu Glu Ile Tyr Ser Asn Lys Glu Lys Leu Ser Arg Phe
305                 310                 315                 320

Arg Glu Val Leu Leu Asn Thr Met Leu Thr Cys Lys Asp His Trp Ser
                325                 330                 335

```
Lys Tyr Phe Asp Glu Asn Asp Lys Leu Ile Lys Ser Lys Leu Leu Tyr
                340                 345                 350

Ser Tyr Leu Asp Arg Trp Arg Tyr Tyr Phe Glu Asn Glu Ser Val Lys
            355                 360                 365

Ser Ala Val Tyr Ser Leu Ile Gly Asn Leu Glu Asn Val Lys Ile Pro
        370                 375                 380

Pro Trp Leu Val Ser Gln Tyr Phe Pro Ser Gln Tyr Gln Lys Met Arg
385                 390                 395                 400

Lys Lys Asp Leu Lys Asn Gly Ala Ala Asp Leu Ile Leu Asp Lys Ile
                405                 410                 415

Gly Glu Val Ile Asp His Tyr Val Tyr Ala Val Lys Glu
                420                 425
```

```
<210> SEQ ID NO 20
<211> LENGTH: 1290
<212> TYPE: DNA
<213> ORGANISM: Unknown
<220> FEATURE:
<223> OTHER INFORMATION: Caldicellulosiruptor kronotskyensis
<220> FEATURE:
<221> NAME/KEY: gene
<222> LOCATION: (1)..(1290)
<223> OTHER INFORMATION: Tagatose-biphosphate aldolase

<400> SEQUENCE: 20
atgagtcctc aaaatccatt gattggttta tttaagaata gagaaaaaga gtttaagggt      60
attatttcag tttgttcttc aaatgaaata gtcttagaag cagttttaaa aagaatgaaa     120
gatacaaacc taccaattat tattgaagcc acagcgaacc aggtaaatca atttggcggg     180
tattctgggt tgacaccgtc tcagttcaaa gaacgagtta taaaaattgc tcaaaaagtt     240
gattttccac ttgagagaat aattcttggt ggggaccatc ttggaccatt tgtgtggcgt     300
gaccaggaac cagaaattgc tatggagtat gctaagcaaa tgataaaaga atacataaaa     360
gcaggtttta ccaaaattca catcgacacg agtatgcctt aaaaggggaa gaacagcata     420
gatgatgaaa taattgctaa agaactgctg tgctctgcag ggattgcgga ggagtgtttt     480
gagaagattt ctataaacaa tccctatatt acaaggccag tttatgtgat aggagctgat     540
gtgccacctc ccggcggaga gtcttctatt tgtcaaacaa ttactactaa agatgaatta     600
gaaagaagtt tagaatattt caaagaagca tttaaaaagg aaggaattga gcatgtattc     660
gattatgtag ttgctgttgt tgcaaatttt ggagttgaat ttgggagcga tgaaattgtt     720
gattttgata tggaaaaagt aaagccgcta aaagaacttt tggcaaagta caatatagta     780
tttgaaggcc attctacaga ttatcaaaca aaagaaaact taaaaagaat ggtcgaatgt     840
ggtattgcaa ttttaaaggt tggtcctgct ctaacattta cattgcgcga agcgttagta     900
gcacttagtc atattgaaga gaaatttatt agcaatgaaa aggagaaaact gtcaagattt     960 agagaagttt tattgaatac tatgctaaca tgcaaagatc actggagtaa atattttgat    1020
gagaatgata agttaattaa gtcaaagctc ctatatagct atcttgacag atggagatac    1080
tattttgaaa acgagagtgt gaaaagtgct gtttattctc ttattggaaa tttagagaat    1140
gttaaaattc caccttggct tgtaagtcag tattttcctt ctcagtacca aaagatgaga    1200 aaaaagatt taaaaaacgg tgctgccgac ctaatattgg ataaaatagg ggaagtcatt    1260
gaccattatg tttatgcggt aaaagaataa                                    1290
```

```
<210> SEQ ID NO 21
<211> LENGTH: 408
```

```
<212> TYPE: PRT
<213> ORGANISM: Unknown
<220> FEATURE:
<223> OTHER INFORMATION: Caldilinea aerophila
<220> FEATURE:
<221> NAME/KEY: PEPTIDE
<222> LOCATION: (1)..(408)
<223> OTHER INFORMATION: Tagatose-biphosphate aldolase

<400> SEQUENCE: 21
```

Met Ser Thr Leu Arg His Ile Ile Leu Arg Leu Ile Glu Leu Arg Glu
1               5                   10                  15

Arg Glu Gln Ile His Leu Thr Leu Leu Ala Val Cys Pro Asn Ser Ala
            20                  25                  30

Ala Val Leu Glu Ala Ala Val Lys Val Ala Ala Arg Cys His Thr Pro
        35                  40                  45

Met Leu Phe Ala Ala Thr Leu Asn Gln Val Asp Arg Asp Gly Gly Tyr
    50                  55                  60

Thr Gly Trp Thr Pro Ala Gln Phe Val Ala Glu Met Arg Arg Tyr Ala
65                  70                  75                  80

Val Arg Tyr Gly Cys Thr Thr Pro Leu Tyr Pro Cys Leu Asp His Gly
                85                  90                  95

Gly Pro Trp Leu Lys Asp Arg His Ala Gln Glu Lys Leu Pro Leu Asp
            100                 105                 110

Gln Ala Met His Glu Val Lys Leu Ser Leu Thr Ala Cys Leu Glu Ala
        115                 120                 125

Gly Tyr Ala Leu Leu His Ile Asp Pro Thr Val Asp Arg Thr Leu Pro
    130                 135                 140

Pro Gly Glu Ala Pro Leu Val Pro Ile Val Val Glu Arg Thr Val Glu
145                 150                 155                 160

Leu Ile Glu His Ala Glu Gln Glu Arg Gln Arg Leu Asn Leu Pro Ala
                165                 170                 175

Val Ala Tyr Glu Val Gly Thr Glu Glu Val His Gly Gly Leu Val Asn
            180                 185                 190

Phe Asp Asn Phe Val Ala Phe Leu Asp Leu Leu Lys Ala Arg Leu Glu
        195                 200                 205

Gln Arg Ala Leu Met His Ala Trp Pro Ala Phe Val Val Ala Gln Val
    210                 215                 220

Gly Thr Asp Leu His Thr Thr Tyr Phe Asp Pro Ser Ala Ala Gln Arg
225                 230                 235                 240

Leu Thr Glu Ile Val Arg Pro Thr Gly Ala Leu Leu Lys Gly His Tyr
                245                 250                 255

Thr Asp Trp Val Glu Asn Pro Ala Asp Tyr Pro Arg Val Gly Met Gly
            260                 265                 270

Gly Ala Asn Val Gly Pro Glu Phe Thr Ala Ala Glu Phe Glu Ala Leu
        275                 280                 285

Glu Ala Leu Glu Arg Arg Glu Gln Arg Leu Cys Ala Asn Arg Lys Leu
    290                 295                 300

Gln Pro Ala Cys Phe Leu Ala Ala Leu Glu Glu Ala Val Val Ala Ser
305                 310                 315                 320

Asp Arg Trp Arg Lys Trp Leu Gln Pro Asp Glu Ile Gly Lys Pro Phe
                325                 330                 335

Ala Glu Leu Thr Pro Ala Arg Arg Trp Leu Val Gln Thr Gly Ala
            340                 345                 350

Arg Tyr Val Trp Thr Ala Pro Lys Val Ile Ala Ala Arg Glu Gln Leu
    355                 360                 365

Tyr Ala His Leu Ser Leu Val Gln Ala Asp Pro His Ala Tyr Val Val
        370                 375                 380

Glu Ser Val Ala Arg Ser Ile Glu Arg Tyr Ile Asp Ala Phe Asn Leu
385                 390                 395                 400

Tyr Asp Ala Ala Thr Leu Leu Gly
                405

<210> SEQ ID NO 22
<211> LENGTH: 1227
<212> TYPE: DNA
<213> ORGANISM: Unknown
<220> FEATURE:
<223> OTHER INFORMATION: Caldilinea aerophila
<220> FEATURE:
<221> NAME/KEY: gene
<222> LOCATION: (1)..(1227)
<223> OTHER INFORMATION: Tagatose-biphosphate aldolase

<400> SEQUENCE: 22

```
atgtcaacac ttcgccacat cattttgcga ctgatcgagc tgcgtgaacg agaacagatc      60
catctcacgc tgctggccgt ctgtcccaac tcggcggcgg tgctggaggc agcggtgaag     120
gtcgccgcgc gctgccacac gccgatgctc ttcgctgcca cgctcaatca agtcgatcgc     180
gacggcggct acaccggttg gacgcctgcg caattcgtcg ccgagatgcg tcgctatgcc     240
gtccgctatg gctgcaccac cccgctctat ccttgcctgg atcacggcgg ccgtggctc      300 aaagatcgcc atgcacagga aaagctaccg ctcgaccagg cgatgcatga ggtcaagctg     360
agcctcaccg cctgtctgga ggccggctac gcgctgctgc acatcgaccc cacggtcgat     420
cgcacgctcc cgcccggaga agcgccgctc gtgccgatcg tcgtcgagcg cacggtcgag     480
ctgatcgaac atgccgaaca ggagcgacag cggctgaacc tgccggcggt cgcctatgaa     540
gtcggcaccg aagaagtaca tggcgggctg gtgaatttcg acaattttgt cgccttcttg     600
gatttgctca aggcaaggct tgaacaacgt gccctgatgc acgcctggcc cgccttcgtg     660
gtggcgcagg tcggcactga cctgcataca acgtattttg accccagtgc ggcgcaacgg     720
ctgactgaga tcgtgcgccc taccggtgca ctgttgaagg gcactacac cgactgggtc      780 gaaaatcccg ccgactatcc gagggtaggc atgggaggcg ccaacgttgg tccagagttt     840
acggcggccg agttcgaggc gctgaagcg ctggaacggc gggaacaacg gctgtgcgcc      900
aaccggaaat tgcagcccgc ctgttttttg gctgcactgg aagaggcagt agtcgcttca     960
gatcgttggc ggaagtggct ccagcccgat gagatcggca agccctttgc agaattaacg    1020
cccgcacgcc ggcgctggct cgtgcagacc ggggcacgct acgtctggac tgcgccgaaa    1080
gttatcgccg cacgcgaaca gctctatgcg cacctctccc ttgtgcaggc ggatccacat    1140
gcctacgtgg tagagtcagt cgcccggtca atcgagcgct atatcgatgc cttcaactta    1200
tacgacgccg ctacattgct tggatga                                        1227
```

<210> SEQ ID NO 23
<211> LENGTH: 446
<212> TYPE: PRT
<213> ORGANISM: Unknown
<220> FEATURE:
<223> OTHER INFORMATION: Thermoanaerobacter thermohydrosulfuricus
<220> FEATURE:
<221> NAME/KEY: PEPTIDE
<222> LOCATION: (1)..(446)
<223> OTHER INFORMATION: Tagatose-biphosphate aldolase

<400> SEQUENCE: 23

-continued

```
Met Asn Thr Glu His Pro Leu Lys Asn Val Val Lys Leu Gln Lys Lys
1               5                   10                  15

Gly Ile Pro Ile Gly Ile Tyr Ser Val Cys Ser Ala Asn Glu Ile Val
            20                  25                  30

Ile Gln Val Ala Met Glu Lys Ala Leu Ser Met Asp Ser Tyr Val Leu
        35                  40                  45

Ile Glu Ala Thr Ala Asn Gln Val Asn Gln Tyr Gly Gly Tyr Thr Asn
50                  55                  60

Met Lys Pro Ile Asp Phe Arg Asp Phe Val Tyr Ser Ile Ala Lys Arg
65                  70                  75                  80

Ile Asn Phe Pro Glu Asn Arg Ile Ile Leu Gly Gly Asp His Leu Gly
                85                  90                  95

Pro Leu Pro Trp Lys Asn Gln Gln Ala Lys Lys Ala Met Glu Glu Ala
            100                 105                 110

Lys Glu Leu Val Lys Gln Phe Val Met Ala Gly Phe Thr Lys Ile His
        115                 120                 125

Val Asp Thr Ser Met Leu Leu Gly Asp Asp Asn Ile Asn Ile Lys Leu
    130                 135                 140

Asp Thr Glu Thr Ile Ala Glu Arg Gly Ala Ile Leu Val Ser Val Ala
145                 150                 155                 160

Glu Arg Ala Phe Glu Glu Leu Lys Lys Phe Asn Pro Tyr Ala Leu His
                165                 170                 175

Pro Val Tyr Val Ile Gly Ser Glu Val Pro Val Pro Gly Gly Ser Gln
            180                 185                 190

Lys Glu Asn Asn Asn Glu Ile Gln Val Thr Lys Pro Thr Asp Phe Glu
        195                 200                 205

Glu Thr Val Glu Val Tyr Lys Ser Thr Phe Tyr Lys Tyr Gly Leu Gly
    210                 215                 220

Asn Ala Trp Glu Asp Val Val Ala Val Val Gln Ala Gly Val Glu
225                 230                 235                 240

Phe Gly Val Glu Asp Ile His Glu Tyr Asp His Gln Ala Glu Asn
                245                 250                 255

Leu Val Ser Ala Leu Lys Lys Tyr Pro Asn Leu Val Phe Glu Ala His
            260                 265                 270

Ser Thr Asp Tyr Gln Pro Ala Lys Leu Leu Lys Glu Met Val Arg Asp
        275                 280                 285

Gly Phe Ala Ile Leu Lys Val Gly Pro Glu Leu Thr Phe Ala Leu Arg
    290                 295                 300

Glu Gly Leu Phe Ala Leu Asn Ile Ile Glu Lys Glu Leu Phe Lys Asp
305                 310                 315                 320

Asn His Asp Ile Glu Met Ser Asn Phe Ile Asp Ile Leu Asp Thr Ala
                325                 330                 335

Met Leu Asn Asn Pro Lys Tyr Trp Glu Gln Tyr Tyr Tyr Gly Asp Asp
            340                 345                 350

Asn Lys Ile Arg Ile Ala Arg Lys Tyr Ser Tyr Ser Asp Arg Cys Arg
        355                 360                 365

Tyr Tyr Leu Ile Glu Asn Glu Val Arg Ala Ser Met Ser Arg Leu Phe
    370                 375                 380

Lys Asn Leu Thr Asn Val Glu Ile Pro Leu Thr Leu Ile Ser Gln Tyr
385                 390                 395                 400

Met Pro Ile Gln Tyr Glu Lys Ile Arg Met Gly Leu Leu Lys Asn Asp
                405                 410                 415
```

```
Pro Glu Asn Leu Val Lys Asp Lys Ile Gly Asn Cys Ile Asp Lys Tyr
            420                 425                 430

Leu Tyr Ala Thr Asn Pro Thr Ser Gly Glu Phe Lys Leu Ile
        435                 440                 445

<210> SEQ ID NO 24
<211> LENGTH: 1341
<212> TYPE: DNA
<213> ORGANISM: Unknown
<220> FEATURE:
<223> OTHER INFORMATION: Thermoanaerobacter thermohydrosulfuricus
<220> FEATURE:
<221> NAME/KEY: gene
<222> LOCATION: (1)..(1341)
<223> OTHER INFORMATION: Tagatose-biphosphate aldolase

<400> SEQUENCE: 24
atgaatacag aacatccttt gaaaaacgtt gttaaactac aaaaaaaggg aattccaata      60
ggtatttatt cagtttgtag tgcaaatgaa atagttattc aagttgcaat ggagaaggca     120
ttgagtatgg atagttatgt tttaattgaa gcaacggcta atcaagtaaa tcaatatggt     180
ggctatacga atatgaaacc tattgatttt agagattttg tgtattctat agccaaaagg     240
ataaacttcc cagaaaatag aataatcctt ggcggggacc acttaggacc tttgccatgg     300
aaaaatcaac aagcgaaaaa agcaatggaa gaagcaaaag aacttgttaa acaatttgtg     360
atggctggct ttacgaaaat tcatgtagat acaagtatgc ttcttggaga tgataacata     420
aatatcaaac tagatactga aactattgcg gagagaggag cgatacttgt atcagtagca     480
gaaagagctt ttgaggagtt aaaaaagttt aatccttatg ctcttcatcc agtttatgta     540
ataggtagtg aagttcctgt tccaggaggt tctcaaaaag aaaataataa tgaaatacaa     600
gtaacaaagc cgacggattt tgaagaaact gtggaagtgt ataaaagcac tttctataaa     660
tatggtttag gaaacgcatg ggaagatgtt gtagcagtgg ttgtgcaggc tggggtggaa     720
tttggagttg aagatattca tgaatatgat caccaacagg ctgaaaattt agtaagtgct     780
ttaaaaaagt atcctaattt agtatttgaa gcccactcta cggattatca acctgcaaaa     840
ctactaaaag aaatggtgag agatggattt gctatactta agttggacc tgaattgact     900 tttgcattaa gggaaggatt gtttgctctg aatattatag aaaaagaatt atttaaagat     960
aatcatgata ttgagatgtc aaattttatt gatatccttg atacagcaat gttaaataat    1020
ccgaagtatt gggaacagta ttattacggt gatgataata aaattagaat tgctagaaaa    1080
tacagctatt ctgatagatg taggtattat ctaatcgaaa atgaagttag agcatctatg    1140
tctaggttgt ttaaaaattt aacaaatgtt gagataccat taaccttgat aagtcagtat    1200
atgcctattc aatatgaaaa aattagaatg ggactattaa aaaatgatcc tgagaattta    1260
gtaaaagata aaattggaaa ttgcattgat aagtatttgt atgctactaa tccgacaagt    1320
ggagaattta aactaatata a                                              1341
```